(12) United States Patent
Arrowsmith et al.

(10) Patent No.: US 6,215,044 B1
(45) Date of Patent: Apr. 10, 2001

(54) TOMATO XYLOGLUCAN ENDO-TRANSGLYCOSYLASE NUCLEIC ACIDS

(75) Inventors: David A. Arrowsmith, Rushden; Susan A. Hellyer, Huntingdon; Jacqueline de Silva, Pavenham; Sally A. Whiteman, Goldington, all of (GB)

(73) Assignee: Unilever Patent Holdings B.V., Vlaardingen (NE)

( * ) Notice: Subject to any disclaimer, the term of this patent is extended or adjusted under 35 U.S.C. 154(b) by 0 days.

(21) Appl. No.: 08/640,737

(22) PCT Filed: Nov. 10, 1994

(86) PCT No.: PCT/GB94/02467

§ 371 Date: May 6, 1996

§ 102(e) Date: May 6, 1996

(87) PCT Pub. No.: WO95/13384

PCT Pub. Date: May 18, 1995

(30) Foreign Application Priority Data

Nov. 10, 1993 (GB) .................................................. 9323225

(51) Int. Cl.[7] ............................... A01H 5/00; C12N 1/21; C12N 5/14; C12N 15/29; C12N 15/52; C12N 15/74; C12N 15/82

(52) U.S. Cl. ..................... 800/298; 435/69.1; 435/252.3; 435/254.2; 435/320.1; 435/419; 435/468; 435/477; 435/483; 536/23.2; 536/23.6; 800/278; 800/286

(58) Field of Search ................................. 536/23.2, 23.6; 435/172.3, 419, 320.1, 243, 254.2, 183, 69.1, 252.3, 468, 477, 483; 800/205, 278, 286, 298

(56) References Cited

U.S. PATENT DOCUMENTS 5,767,364 * 6/1998 De Silva et al. ..................... 800/205

FOREIGN PATENT DOCUMENTS

| 562836 | * | 9/1993 | (EP) . |
| 562 836 | | 9/1993 | (EP) . |
| WO 93/17101 | * | 9/1993 | (WO) . |
| 93/17101 | | 9/1993 | (WO) . |

OTHER PUBLICATIONS

Medford JI, et al. "Molecular cloning and characterization of genes expressed in shoot apical meristems." Plant Cell 3:359–370, Apr. 1991.*

De Silva J, et al. "Molecular characterization of a xyloglucan–specific endo–(1–>4)–B–D–glucanase (xyloglucan endo–transglycosylase) from nasturtium seeds." Plant Journal 3: 701–711, 1993.*

Stam M, et al. "The silence of genes in transgenic plants." Ann. Bot. 79:3–12, 1997.*

Koziel MG, et al. "Optimizing expression of transgenes with an emphasis on post–transcriptional events." Plant Mol. Biol. 32:393–405, 1996.*

Smith CJS, et al. "Antisense RNA inhibiton of polygalacturonase gene expression in transgenic tomatoes." Nature 334: 724–726, Aug. 25, 1988.*

(List continued on next page.)

Primary Examiner—Amy J. Nelson
(74) Attorney, Agent, or Firm—Pillsbury Winthrop LLP

(57) ABSTRACT

Disclosed are nucleic acids from tomato encoding polypeptides having xyloglucan endo-transglycosylase (XET) activity, comprising residues 21–289 of the amino acid sequence shown in FIG. 1 (SEQ ID NO:2) or or comprising residues 19–287 of the amino acid sequence shown in FIG. 5 (SEQ ID NO:8), and transgenic plants comprising said nucleic acids.

24 Claims, 17 Drawing Sheets

OTHER PUBLICATIONS

DeBlock M. The cell biology of plant tranformation: Current state, problems, prospects and the implications for the plant breeding. Euphytica 71: 1–14, 1993.*

De Silva et al: "Molecular characterization of a xyloglucan-specific endo-(1–4)-beta-D-glucanase (xyloglucan endo-transflycosylase) from nasturtium seeds", The Plant Journal, vol. 3, No. 5, May 1993 pp. 701–7111, see the whole document.

Maclachlan, et al: "Multiple forms of 1,4–beta glucanase in ripening tomato fruits include a xyloglucanase activatible by xyloglucan oligosccharadies", Database Biosis Biosciences Information Service, DN BA93:138777 see abstract & Aust.J.Plant Physiol., vol. 19, No. 2, 1992, pp. 137–146.

Medford, et al: "Molecular cloning and characterization of genes expressed in shoot apical meristems", see figure 3, The Plant Cell, vol. 3, 1991, pp. 359–370.

EMBL Sequence Database Entry L22162 Release 36, 23–7–93, Glycine max brassinosteroid–regulated protein, mRNA, complete cds., 1993.

Xu et al. The Arabidopsis XET–related gene family: Environmental and hormonal regulation of expression, Plant Journal, 9(6), 879–889 (1996).

Smith et al. The regulation of leaf elongation and xyloglucan endotransglycosylase by gibberellin in 'Himalaya' barley (Hordeum vulgare L), Journal of Experimental Botany, 47 (302), 1395–1404 (1996) abstract only.

* cited by examiner

Fig. 1A

```
GAAGTAGACGATGCAGCTGGAATTTCAAAACATACATTCCCAAAAACAACTAACTACATAT
TCCTTAAGATTTCCTATAATGTTGCTGCAGCTATCGTTCTGTTCTTGCTTCTACTTCTTTG
              M  L  L  Q  Q  L  S  V  L  A  L  L  L  L
                         ^5                        ^10

CTATGTCCTGTGTTTGGGCTGACAATTTCTACCAAGATGCAACGGTTACCTTTGGTGATCAG
 L  C  P  V  W  A  D  N  F  Y  Q  D  A  T  V  T  F  G  D  Q
   ^15                       ^20                       ^25                ^30

CGAGCTCAGATACAAGATGGTGGGCGCCTTCTCGCCCTTGTCCCTTGACAAAATTTCAGT
 R  A  Q  I  Q  D  G  G  R  L  L  A  L  S  L  D  K  I  S  G
       ^35                       ^40                       ^45                ^50

TCAGGATTTCAGTCTAAGAATGAATATTTATTTGGAAGGTTCGATATGCAGCTCAAACTA
 S  G  F  Q  S  K  N  E  Y  L  F  G  R  F  D  M  Q  L  K  L
       ^55                       ^60                       ^65                ^70

GTACCTGGAAATTCTGCTGGCACTGTCACTTTCTATTGTCTTCTCAAGGAGCAGG
 V  P  G  N  S  A  G  T  V  T  F  Y  L  S  S  Q  G  A  G
       ^75                       ^80                       ^85                ^90

CACGACGAAATTGATTTTGAGTTTCTGGGAAATTCATCAGGCCAACCGTACACGGTTCAT
 H  D  E  I  D  F  E  F  F  L  G  N  S  S  G  Q  P  Y  T  V  H
       ^95                       ^100                      ^105               ^110

ACTAATGTCTACTCTCAAGGAAAAGGCAACAAAGAACAACAGTTTCGCCTATGGTTTGAT
 T  N  V  Y  S  Q  G  K  G  N  K  E  Q  Q  F  R  L  W  F  D
       ^115                      ^120                      ^125               ^130

CCCACCTCGCCGTTCCACACTTACTCTATTGTTTGGAACTCTCAAGCATCATATTTTTG
 P  T  S  P  F  H  T  Y  S  I  V  W  N  S  Q  R  I  F  L
       ^135                      ^140                      ^145               ^150
```

Fig. 1B

```
GTGGATAATATCCCAATAAGAGTATTCAACAACCACGAAAAGCTTGGTGTGTTGCATTCCCA
 V  D  N  I  P  I  R  V  F  N  N  H  E  K  L  G  V  A  F  P
   ^155           ^160              ^165              ^170

AAGAACCAAGCAATGAGAGTTTATGCCAGTTTATGGAATGCTGATGATGACTGGGCAACACAA
 K  N  Q  A  M  R  V  Y  A  S  L  W  N  A  D  D  W  A  T  Q
   ^175           ^180              ^185              ^190

GGAGGGCGAGTGAAGAAGACGGATTGGTCAATGGCTCCGTTTACAGCTTCTTACAGGAATTC
 G  G  R  V  K  K  T  D  W  S  M  A  P  F  T  A  S  Y  R  N  F
   ^195           ^200              ^205              ^210

AACACAAATGCTTGTGTTTGGTCAGCTGCATCGTCAGCTACTTCGTCCTGTGGAGGCTCTAAG
 N  T  N  A  C  V  W  S  A  A  S  S  T  S  S  C  G  G  S  K
   ^215           ^220              ^225              ^230

ACTGATTCAGTAAACAATGATCAGGCAGAAACTCAAGAACTGAACGGTAATGACAGA
 T  D  S  V  N  N  D  Q  A  E  T  Q  E  L  N  G  N  D  R
   ^235           ^240              ^245              ^250

AATAGGCTTCGATGGGTTCAGCAGAAATACATGATCTACAATTACTGTGCAGATGCTAAA
 N  R  L  R  W  V  Q  Q  K  Y  M  I  Y  N  Y  C  A  D  A  K
   ^255           ^260              ^265              ^270

AGGTTCTCTCAAGGCCCTTTCTCCCTGAATGCAAACGTTCAAGGTTCTAAAGGATCAAATCT
 R  F  S  Q  G  L  S  P  E  C  K  R  S  R  F
   ^275           ^280              ^285              ^290

ACGAATGTTGTCTGTAATATTATCCCCGGAATTCC
```

Fig. 2

```
Tom3   DEMDLEFLGNLSGDPYTLHTNVFSQGKGN         REQQFHLWFDPT
Tom1   DEIDDFEFLGNVSGQPYTIHTNVYYTQGKGN       KEQQFHLWFDPT
Meri5  DEIDDFEFLGNMSGDPYTLHTNVYYTQGKGD       KEQQFHLWFDPT
XET    DEIDIEFLGTIPGKPYTLQTNVFIEGSGDYNIIGRELRIHLWFDPT
```

Fig. 3D

| | | |
|---|---|---|
| 8-TH: | CGATGCAGCTGGAATTTCA | (SENSE) |
| 8-TB: | AGTTTGAGCTGCATATCGAA | (ANTISENSE) |
| 8-HS: | TTTGATCCCACCTCGCCGTT | (SENSE) |
| 8-HT: | CAGCTGACCAAACACAAGCA | (ANTISENSE) |

Fig. 4D

| | |
|---|---|
| 16-1: | AATTATCAGCGGAAACAGGG |
| 16-1R: | CCCTGTTTCCGCTGATAATT |
| 16-2: | CTATTAGCATCTGCACAGTA |
| 16-2R: | TACTGTGCAGATGCTAATAG |
| 16-3R: | GGAGGACGGGTGAAGACAGA |
| 16-4: | GTGTAAGGTAGTCCTGATGA |
| 16-4R: | TCATCAGGACTACCTTACAC |

Fig. 5A

```
GAATTCGGGTAGGCTTTGGTTGCAATAAGCCGTCTGTTCTTGCTTACTAC
TTTGGAAAAATTGACTTTAGGCCTGCGGTCCCTAGCATTAAATTCATCGACCGCTGTGTC
ATATAGACGCCGCTTTGCAAGATCGTTGACCAGGTTATGTTACCTCGGACGGTCTCAAG
CAAGGCGGACGATGTGGCTGTGTTGTGTGTATGCCATTGTAGTTGTAGAATGTAAAATATA

ATGGTGCTGCAGCTTCTCTTCTCTTACACTAGTCTTGTCCTTTCCCCGTTCCGCTGATAAT
 M  L  Q  L  S  L  T  L  V  L  L  S  P  V  S  A  D  N
             ^5              ^10             ^15

TTCTACCAAGACGCGGCGGTCACGTTTGGTGACCAGCGCTCAGATACAAGATGGAGG
 F  Y  Q  D  A  A  V  T  F  G  D  Q  R  A  Q  I  Q  D  G  G
             ^25             ^30             ^35

CGCCTTCTCACATTGTCACTTGATAAATTTCAGTTCCGGATTTCAGTCTAAGAATGAG
 R  L  L  T  L  S  L  D  K  I  S  G  S  G  F  Q  S  K  N  E
             ^45             ^50             ^55

TATTTATTCGGAAGGTTCGATATGCAGCTTAAACTCGTACCTGGAAATTCTGCTGGCACT
 Y  L  F  G  R  F  D  M  Q  L  K  L  V  P  G  N  S  A  G  T
             ^65             ^70             ^75

GTCACCACATTCTATTGTCTCTCTCAAGGAGCAGGGCATGATGAAATTGATTTGAGTTT
 V  T  T  F  Y  L  S  S  Q  G  A  G  H  D  E  I  D  F  E  F
             ^85             ^90             ^95

CTAGGAAATTCATCAGGACTACCTTGCATACACGGTTCATACCAATGTTACTCTCAAGGAAAA
 L  G  N  S  S  G  L  P  Y  T  H  T  N  V  Y  S  Q  G  K
             ^105            ^110            ^115

GGCAATAAAGAACAACAATTTCGTCTCTGGTTTGATCCAACTTCGTTCCACACTTAC
 G  N  K  E  Q  Q  F  R  L  W  F  D  P  T  S  S  F  H  T  Y
             ^125            ^130            ^135

TCTATTGTTTGGAACTCTCAAGGATCATATTTTTGGTGGATAATATCCCAATTAGAGTG
 S  I  V  W  N  S  Q  R  I  I  F  L  V  D  N  I  P  I  R  V
             ^145            ^150            ^155
```

Fig. 5B

```
TTCAACAACCACGAAGCACTTGGTGTGTTGCATACCCAAAGAATCAAGCAATGAGAGTTTAC
 F  N  N  H  E  A  L  G  V  A  Y  P  K  N  Q  A  M  R  V  Y
                   ^165              ^170              ^175
GCGAGTCTATGGAATGCTGATGATTGGGCTACACAAGGAGGACGGGTGAAGACAGATTGG
 A  S  L  M  N  A  D  D  W  A  T  Q  G  G  R  V  K  T  D  W
           ^185              ^190              ^195
TCTATGGCTCCGTTCACAGCTTCTTACAGGAATTTCAATACAAATGCTTGTGTTTGGTCA
 S  M  A  P  F  T  A  S  Y  R  N  F  N  T  N  A  C  V  W  S
           ^205              ^210              ^215
GCTGCTACGTCTACTTCGTCTTGTGGAGGTTCTAAGACTGAGTCAGTAAACAATGATGAG
 A  A  T  S  S  C  G  G  S  K  T  E  S  V  N  N  D  E
           ^225              ^230              ^235
ACATGGCAAAACGCAACAACTACAATTACTGTGCAGATGCTAATAGGTTCTCTCAAGGATGGGTTCAGCAG
 T  W  Q  Q  L  N  A  N  G  R  N  R  I  R  W  V  Q  Q
           ^245              ^250              ^255
AAGTACATGATCTACAATTACTGTGCAGATGCTAATAGGTTCTCTCAAGGCTTTTCTCCT
 K  Y  M  I  Y  N  Y  C  A  D  A  N  R  F  S  Q  G  F  S  P
           ^265              ^270              ^275
GAATGCAAGCGTTCAAGGTTCTAAGGCGGATATATAGTATATGAATGTAAAATTATGT
 E  C  K  R  S  R  F
           ^285
TTGTTTCACTTTTCTATTCTTTTAATTTTGATCAGGTAAAAAAAAAAGAACATAGTGT
AATTATTTGTGTATGCAATATATTCTTTATTCTTTTTGTTAATCATGAAATAGAAATAATA
ATGAATTGTTTTCCTGAAAAAAAAAAAACCGGAATTCC
```

Fig. 6A

Tomato XET cDNA (B1) and encoded amino acid sequences (B1 & B2)

```
     TCCTTAAGATTTCCTATAATGTGCTGCAGCAGCTATCTGTTCTTGCTCTACTTCTCTTG
B1                     M  L  L  Q  Q  L  S  V  L  A  L  L  L  L
B2                              L  .  T  V  .

CTATGTCCTGTGTTTGGGCTGACAATTTCTACCAAGATGGTGACGCAACGGTTACCTTTGGTGATCAG
B1   L  C  P  V  W  A  D  N  F  Y  Q  D  A  T  V  T  F  G  D  Q
B2   -  S  .  .  .  .  S  .  .  .  .  .  .  A  .  .  .  .  .  .

CGAGCTCAGATACAAGATGGTGGGCGCCTTCTCGCCTTGTCCCTTGACAAAATTTCAGGT
B1   R  A  Q  I  Q  D  G  G  R  L  L  A  L  S  L  D  K  I  S  G
B2                                              T

TCAGGATTTCAGTCTAAGAATGAATATTTATTTGGAAGGTTCGATATGCAGCTCAAACTA
B1   S  G  F  Q  S  K  N  E  Y  L  F  G  R  F  D  M  Q  L  K  L

GTACCTGGAAATTCTGCTGGCACTGTCACTACCTTCTATTGTCTCTCAAGGAGCAGGG
B1   V  P  G  N  S  A  G  T  V  T  T  F  Y  L  S  S  Q  G  A  G

CACGACGAAATTGATTTTGAGTTTCTTGGAAATTCATCAGGCCAACCGTACACGGTTCAT
B1   H  D  E  I  D  F  E  F  L  G  N  S  S  G  Q  P  Y  T  V  H
B2                                              L

ACTAATGTCTACTCTCAAGGAAAAGGCAACAAAGAACAACAGTTTCGCCTATGGTTTGAT
B1   T  N  V  Y  S  Q  G  K  G  N  K  E  Q  Q  F  R  L  W  F  D

CCCACCTCGCCGTTCCACACTACTCTATTGTTGGAACTCTCAACGCATCATATTTTTG
B1   P  T  S  P  F  H  T  Y  S  I  V  W  N  S  Q  R  I  I  F  L
B2         S
```

Fig. 6B

```
GTGGATAATATCCCAATAAGAGTATTCAACAACCACGAAAAGCTTGGTGTTGCATTCCCA
 V  D  N  I  P  I  R  V  F  N  N  H  E  K  L  G  V  A  F  P
                                           .  A            .  Y

AAGAACCAAGCAATGAGAGTTTATGCCAGTTTATGGAATGCTGATGACTGGGCAACACAA
 K  N  Q  A  M  R  V  Y  A  S  L  W  N  A  D  D  W  A  T  Q
                                           .

GGAGGGCGAGTGAAGACGGATTGGTCCGTTACAGCTCCGTTACAGCTCTTACAGGAATTC
 G  G  R  V  K  T  D  W  S  M  A  P  F  T  A  S  Y  R  N  F
                           .                             .

AACACAAATGCTTGTGTTTGGTCAGCTGCATCGTCTACTTCGTCCTGTGGAGGCTCTAAG
 N  T  N  A  C  V  W  S  A  A  S  T  S  S  C  G  G  S  K
                           .        T

ACTGATTCAGTAAACAATGATCAGGCATGGCAAACTCAAGAACTGAACGGTAATGACAGA
 T  D  S  V  N  N  D  Q  A  W  Q  T  Q  E  L  N  G  N  D  R
    .  E                                                 .  A  .  G

AATAGGCTTCGATGGGTTCAGCAGAAATACATGATCTACAATTACTGTGCAGATGCTAAA
 N  R  L  R  W  V  Q  Q  K  Y  M  I  Y  N  Y  C  A  D  A  K
    .  I

AGGTTCTCTCAAGGCCTTTCTCCTGAATGCAAACGTTCAAGGTTCTAAAGGATCAAATCT
 R  F  S  Q  G  L  S  P  E  C  K  R  S  R  F  X        X
                .  F

ACGAATGTGTCTGTAATATTATCCCGGAATTCC
```

• = IDENTICAL AMINO ACID
◄ = PREDICTED SIGNAL PEPTIDE CLEAVAGE SITE

SITES NOT SHOWN: Dra1, EcoRV, Spe, Not, BstX1

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
        (A) LENGTH: 994 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (ix) FEATURE:
        (A) NAME/KEY: CDS
        (B) LOCATION: 79..945

(xi) SEQUENCE DESCRIPTION: SEQ ID NO: 1:

```
GAAGTAGACG ATGCAGCTGG AATTTCAAAC ATACATTCCC AAAAACAACT AACTACATAT        60

TCCTTAAGAT TTCCTATA ATG TTG CTG CAG CAG CTA TCT GTT CTT GCT CTA        111
                 Met Leu Leu Gln Gln Leu Ser Val Leu Ala Leu
                  1               5                      10

CTT CTC TTG CTA TGT CCT GTT TGG GCT GAC AAT TTC TAC CAA GAT GCA        159
Leu Leu Leu Leu Cys Pro Val Trp Ala Asp Asn Phe Tyr Gln Asp Ala
             15                  20                  25

ACG GTT ACC TTT GGT GAT CAG CGA GCT CAG ATA CAA GAT GGT GGG CGC        207
Thr Val Thr Phe Gly Asp Gln Arg Ala Gln Ile Gln Asp Gly Gly Arg
         30                  35                  40

CTT CTC GCC TTG TCC CTT GAC AAA ATT TCA GGT TCA GGA TTT CAG TCT        255
Leu Leu Ala Leu Ser Leu Asp Lys Ile Ser Gly Ser Gly Phe Gln Ser
```

```
                45                    50                    55
AAG AAT GAA TAT TTA TTT GGA AGG TTC GAT ATG CAG CTC AAA CTA GTA      303
Lys Asn Glu Tyr Leu Phe Gly Arg Phe Asp Met Gln Leu Lys Leu Val
 60              65                  70                  75

CCT GGA AAT TCT GCT GGC ACT GTC ACT ACC TTC TAT TTG TCT TCT CAA      351
Pro Gly Asn Ser Ala Gly Thr Val Thr Thr Phe Tyr Leu Ser Ser Gln
                 80                  85                  90

GGA GCA GGG CAC GAC GAA ATT GAT TTT GAG TTT CTG GGA AAT TCA TCA      399
Gly Ala Gly His Asp Glu Ile Asp Phe Glu Phe Leu Gly Asn Ser Ser
                 95                 100                 105

GGC CAA CCG TAC ACG GTT CAT ACT AAT GTC TAC TCT CAA GGA AAA GGC      447
Gly Gln Pro Tyr Thr Val His Thr Asn Val Tyr Ser Gln Gly Lys Gly
            110                 115                 120

AAC AAA GAA CAA CAG TTT CGC CTA TGG TTT GAT CCC ACC TCG CCG TTC      495
Asn Lys Glu Gln Gln Phe Arg Leu Trp Phe Asp Pro Thr Ser Pro Phe
    125                 130                 135

CAC ACC TAC TCT ATT GTT TGG AAC TCT CAA CGC ATC ATA TTT TTG GTG      543
His Thr Tyr Ser Ile Val Trp Asn Ser Gln Arg Ile Ile Phe Leu Val
140                 145                 150                 155

GAT AAT ATC CCA ATA AGA GTA TTC AAC AAC CAC GAA AAG CTT GGT GTT      591
Asp Asn Ile Pro Ile Arg Val Phe Asn Asn His Glu Lys Leu Gly Val
                160                 165                 170

GCA TTC CCA AAG AAC CAA GCA ATG AGA GTT TAT GCC AGT TTA TGG AAT      639
Ala Phe Pro Lys Asn Gln Ala Met Arg Val Tyr Ala Ser Leu Trp Asn
            175                 180                 185

GCT GAT GAC TGG GCA ACA CAA GGA GGG CGA GTG AAG ACG GAT TGG TCA      687
Ala Asp Asp Trp Ala Thr Gln Gly Gly Arg Val Lys Thr Asp Trp Ser
        190                 195                 200

ATG GCT CCG TTT ACA GCT TCT TAC AGG AAT TTC AAC ACA AAT GCT TGT      735
Met Ala Pro Phe Thr Ala Ser Tyr Arg Asn Phe Asn Thr Asn Ala Cys
    205                 210                 215

GTT TGG TCA GCT GCA TCG TCT ACT TCG TCC TGT GGA GGC TCT AAG ACT      783
Val Trp Ser Ala Ala Ser Ser Thr Ser Ser Cys Gly Gly Ser Lys Thr
220                 225                 230                 235

GAT TCA GTA AAC AAT GAT CAG GCA TGG CAA ACT CAA GAA CTG AAC GGT      831
Asp Ser Val Asn Asn Asp Gln Ala Trp Gln Thr Gln Glu Leu Asn Gly
                240                 245                 250

AAT GAC AGA AAT AGG CTT CGA TGG GTT CAG CAG AAA TAC ATG ATC TAC      879
Asn Asp Arg Asn Arg Leu Arg Trp Val Gln Gln Lys Tyr Met Ile Tyr
            255                 260                 265

AAT TAC TGT GCA GAT GCT AAA AGG TTC TCT CAA GGC CTT TCT CCT GAA      927
Asn Tyr Cys Ala Asp Ala Lys Arg Phe Ser Gln Gly Leu Ser Pro Glu
        270                 275                 280

TGC AAA CGT TCA AGG TTC TAAAGGATCA AATCTACGAA TGTTGTCTGT             975
Cys Lys Arg Ser Arg Phe
    285

AATATTATCC CGGAATTCC                                                 994

(2) INFORMATION FOR SEQ ID NO: 2:

(i) SEQUENCE CHARACTERISTICS:
        (A) LENGTH: 289 amino acids
        (B) TYPE: amino acid
        (D) TOPOLOGY: linear (ii) MOLECULE TYPE: protein (xi) SEQUENCE DESCRIPTION: SEQ ID NO: 2:

Met Leu Leu Gln Gln Leu Ser Val Leu Ala Leu Leu Leu Leu Leu Cys
  1               5                  10                  15
```

```
Pro Val Trp Ala Asp Asn Phe Tyr Gln Asp Ala Thr Val Thr Phe Gly
            20                  25                  30

Asp Gln Arg Ala Gln Ile Gln Asp Gly Gly Arg Leu Leu Ala Leu Ser
        35                  40                  45

Leu Asp Lys Ile Ser Gly Ser Gly Phe Gln Ser Lys Asn Glu Tyr Leu
    50                  55                  60

Phe Gly Arg Phe Asp Met Gln Leu Lys Leu Val Pro Gly Asn Ser Ala
65                  70                  75                  80

Gly Thr Val Thr Thr Phe Tyr Leu Ser Ser Gln Gly Ala Gly His Asp
                85                  90                  95

Glu Ile Asp Phe Glu Phe Leu Gly Asn Ser Ser Gly Gln Pro Tyr Thr
                100                 105                 110

Val His Thr Asn Val Tyr Ser Gln Gly Lys Gly Asn Lys Glu Gln Gln
            115                 120                 125

Phe Arg Leu Trp Phe Asp Pro Thr Ser Pro Phe His Thr Tyr Ser Ile
        130                 135                 140

Val Trp Asn Ser Gln Arg Ile Ile Phe Leu Val Asp Asn Ile Pro Ile
145                 150                 155                 160

Arg Val Phe Asn Asn His Glu Lys Leu Gly Val Ala Phe Pro Lys Asn
                165                 170                 175

Gln Ala Met Arg Val Tyr Ala Ser Leu Trp Asn Ala Asp Asp Trp Ala
                180                 185                 190

Thr Gln Gly Gly Arg Val Lys Thr Asp Trp Ser Met Ala Pro Phe Thr
            195                 200                 205

Ala Ser Tyr Arg Asn Phe Asn Thr Asn Ala Cys Val Trp Ser Ala Ala
        210                 215                 220

Ser Ser Thr Ser Ser Cys Gly Gly Ser Lys Thr Asp Ser Val Asn Asn
225                 230                 235                 240

Asp Gln Ala Trp Gln Thr Gln Glu Leu Asn Gly Asn Asp Arg Asn Arg
                245                 250                 255

Leu Arg Trp Val Gln Gln Lys Tyr Met Ile Tyr Asn Tyr Cys Ala Asp
            260                 265                 270

Ala Lys Arg Phe Ser Gln Gly Leu Ser Pro Glu Cys Lys Arg Ser Arg
        275                 280                 285

Phe (2) INFORMATION FOR SEQ ID NO: 3:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (iii) HYPOTHETICAL: YES (iii) ANTI-SENSE: NO (v) FRAGMENT TYPE: internal (xi) SEQUENCE DESCRIPTION: SEQ ID NO: 3:

Asp Glu Ile Asp Phe Glu Phe Leu Gly Asn
1               5                   10

(2) INFORMATION FOR SEQ ID NO: 4:

(i) SEQUENCE CHARACTERISTICS:
        (A) LENGTH: 10 amino acids
```

(B) TYPE: amino acid
            (D) TOPOLOGY: unknown (ii) MOLECULE TYPE: peptide (iii) HYPOTHETICAL: YES (iii) ANTI-SENSE: NO (v) FRAGMENT TYPE: internal (xi) SEQUENCE DESCRIPTION: SEQ ID NO: 4:

Ser Leu Trp Asn Ala Asp Asp Trp Ala Thr
1               5                   10

(2) INFORMATION FOR SEQ ID NO: 5:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (iii) HYPOTHETICAL: YES (iii) ANTI-SENSE: NO (v) FRAGMENT TYPE: internal (xi) SEQUENCE DESCRIPTION: SEQ ID NO: 5:

Phe Tyr Ser Lys Asn Glu Tyr Leu Phe Gly
1               5                   10

(2) INFORMATION FOR SEQ ID NO: 6:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (iii) HYPOTHETICAL: YES (iii) ANTI-SENSE: NO (v) FRAGMENT TYPE: internal (xi) SEQUENCE DESCRIPTION: SEQ ID NO: 6:

Gly Thr Val Thr Thr Phe Tyr Leu Ser Ser
1               5                   10

(2) INFORMATION FOR SEQ ID NO: 7:

(i) SEQUENCE CHARACTERISTICS:
        (A) LENGTH: 1289 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (ix) FEATURE:
        (A) NAME/KEY: CDS
        (B) LOCATION: 232..1092

(xi) SEQUENCE DESCRIPTION: SEQ ID NO: 7:

-continued

```
GAATTCTGGG TAGGCTTTGG TTGCAATAAG CGTCTGTTCT TCGCTTACTA CTTTGGAAAA      60

ATTGACTTTA GGCCTGCGGT CCCTAGCATT AAATTCATCG ACCGCTGTGT CATATAGACG     120

CCGCTTTGCA AGATCGTTGA CCAAGGTATT GTTACCTCGG ACGGTCTCAA GCAAAGCGGA     180

CGATGTGGCT GTTTGTGTGT ATGCCATTGT AGTTGTAGAA TGTAAAATAT A ATG TTG     237
                                                       Met Leu
                                                         1

CTG CAG CTT TCT CTT CTT ACA CTA GTC TTA CTA TCC CCT GTT TCC GCT      285
Leu Gln Leu Ser Leu Leu Thr Leu Val Leu Leu Ser Pro Val Ser Ala
         5              10              15

GAT AAT TTC TAC CAA GAC GCG GCG GTC ACG TTT GGT GAC CAG CGC GCT      333
Asp Asn Phe Tyr Gln Asp Ala Ala Val Thr Phe Gly Asp Gln Arg Ala
     20              25              30

CAG ATA CAA GAT GGA GGG CGC CTT CTC ACA TTG TCA CTT GAT AAA ATT      381
Gln Ile Gln Asp Gly Gly Arg Leu Leu Thr Leu Ser Leu Asp Lys Ile
 35              40              45              50

TCA GGT TCC GGA TTT CAG TCT AAG AAT GAG TAT TTA TTC GGA AGG TTC      429
Ser Gly Ser Gly Phe Gln Ser Lys Asn Glu Tyr Leu Phe Gly Arg Phe
                 55              60              65

GAT ATG CAG CTT AAA CTC GTA CCT GGA AAT TCT GCT GGC ACT GTC ACC      477
Asp Met Gln Leu Lys Leu Val Pro Gly Asn Ser Ala Gly Thr Val Thr
             70              75              80

ACA TTC TAT TTG TCT TCT CAA GGA GCA GGG CAT GAT GAA ATT GAT TTT      525
Thr Phe Tyr Leu Ser Ser Gln Gly Ala Gly His Asp Glu Ile Asp Phe
         85              90              95

GAG TTT CTA GGA AAT TCA TCA GGA CTA CCT TAC ACG GTT CAT ACC AAT      573
Glu Phe Leu Gly Asn Ser Ser Gly Leu Pro Tyr Thr Val His Thr Asn
     100             105             110

GTT TAC TCT CAA GGA AAA GGC AAT AAA GAA CAA CAA TTT CGT CTC TGG      621
Val Tyr Ser Gln Gly Lys Gly Asn Lys Glu Gln Gln Phe Arg Leu Trp
115             120             125             130

TTT GAT CCA ACT TCG TCG TTC CAC ACT TAC TCT ATT GTT TGG AAC TCT      669
Phe Asp Pro Thr Ser Ser Phe His Thr Tyr Ser Ile Val Trp Asn Ser
             135             140             145

CAA CGG ATC ATA TTT TTG GTG GAT AAT ATC CCA ATT AGA GTG TTC AAC      717
Gln Arg Ile Ile Phe Leu Val Asp Asn Ile Pro Ile Arg Val Phe Asn
         150             155             160

AAC CAC GAA GCA CTT GGT GTT GCA TAC CCA AAG AAT CAA GCA ATG AGA      765
Asn His Glu Ala Leu Gly Val Ala Tyr Pro Lys Asn Gln Ala Met Arg
     165             170             175

GTT TAC GCG AGT CTA TGG AAT GCT GAT GAT TGG GCT ACA CAA GGA GGA      813
Val Tyr Ala Ser Leu Trp Asn Ala Asp Asp Trp Ala Thr Gln Gly Gly
 180             185             190

CGG GTG AAG ACA GAT TGG TCT ATG GCT CCG TTT ACA GCT TCT TAC AGG      861
Arg Val Lys Thr Asp Trp Ser Met Ala Pro Phe Thr Ala Ser Tyr Arg
195             200             205             210

AAT TTC AAT ACA AAT GCT TGT GTT TGG TCA GCT GCT ACG TCT ACT TCG      909
Asn Phe Asn Thr Asn Ala Cys Val Trp Ser Ala Ala Thr Ser Thr Ser
             215             220             225

TCT TGT GGA GGT TCT AAG ACT GAG TCA GTA AAC AAT GAT GAG ACA TGG      957
Ser Cys Gly Gly Ser Lys Thr Glu Ser Val Asn Asn Asp Glu Thr Trp
         230             235             240

CAA ACG CAA CAA CTG AAC GCT AAT GGA AGA AAT AGA ATA CGA TGG GTT     1005
Gln Thr Gln Gln Leu Asn Ala Asn Gly Arg Asn Arg Ile Arg Trp Val
     245             250             255

CAG CAG AAG TAC ATG ATC TAC AAT TAC TGT GCA GAT GCT AAT AGG TTC     1053
Gln Gln Lys Tyr Met Ile Tyr Asn Tyr Cys Ala Asp Ala Asn Arg Phe
 260             265             270

TCT CAA GGC TTT TCT CCT GAA TGC AAG CGT TCA AGG TTC TAAGGCGGAT     1102
Ser Gln Gly Phe Ser Pro Glu Cys Lys Arg Ser Arg Phe
```

```
Ser Gln Gly Phe Ser Pro Glu Cys Lys Arg Ser Arg Phe
275                 280                 285

ATATATAGTA TATGAATGTA AAATTATGTT TGTTTCACTT TTCTATTCTT TTAATTTTGA   1162

TCAGGTAAAA AAAAAAAAGA ACATAGTGTA ATTATTTGTG TATGCAATAT ATTCTTTATT   1222

CTTTTTGTAA TCATGAAATA GAATAATAA TGAATTGTTT TCCTGAAAAA AAAAAAACCG   1282

GAATTCC                                                             1289

(2) INFORMATION FOR SEQ ID NO: 8:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO: 8:

Met Leu Leu Gln Leu Ser Leu Thr Leu Val Leu Ser Pro Val
  1               5                  10                 15

Ser Ala Asp Asn Phe Tyr Gln Asp Ala Ala Val Thr Phe Gly Asp Gln
             20                  25                  30

Arg Ala Gln Ile Gln Asp Gly Gly Arg Leu Leu Thr Leu Ser Leu Asp
         35                  40                  45

Lys Ile Ser Gly Ser Gly Phe Gln Ser Lys Asn Glu Tyr Leu Phe Gly
     50                  55                  60

Arg Phe Asp Met Gln Leu Lys Leu Val Pro Gly Asn Ser Ala Gly Thr
 65                  70                  75                  80

Val Thr Thr Phe Tyr Leu Ser Ser Gln Gly Ala Gly His Asp Glu Ile
                 85                  90                  95

Asp Phe Glu Phe Leu Gly Asn Ser Ser Gly Leu Pro Tyr Thr Val His
                100                 105                 110

Thr Asn Val Tyr Ser Gln Gly Lys Gly Asn Lys Glu Gln Gln Phe Arg
            115                 120                 125

Leu Trp Phe Asp Pro Thr Ser Ser Phe His Thr Tyr Ser Ile Val Trp
    130                 135                 140

Asn Ser Gln Arg Ile Ile Phe Leu Val Asp Asn Ile Pro Ile Arg Val
145                 150                 155                 160

Phe Asn Asn His Glu Ala Leu Gly Val Ala Tyr Pro Lys Asn Gln Ala
                165                 170                 175

Met Arg Val Tyr Ala Ser Leu Trp Asn Ala Asp Asp Trp Ala Thr Gln
                180                 185                 190

Gly Gly Arg Val Lys Thr Asp Trp Ser Met Ala Pro Phe Thr Ala Ser
            195                 200                 205

Tyr Arg Asn Phe Asn Thr Asn Ala Cys Val Trp Ser Ala Ala Thr Ser
    210                 215                 220

Thr Ser Ser Cys Gly Gly Ser Lys Thr Glu Ser Val Asn Asn Asp Glu
225                 230                 235                 240

Thr Trp Gln Thr Gln Gln Leu Asn Ala Asn Gly Arg Asn Arg Ile Arg
                245                 250                 255

Trp Val Gln Gln Lys Tyr Met Ile Tyr Asn Tyr Cys Ala Asp Ala Asn
                260                 265                 270

Arg Phe Ser Gln Gly Phe Ser Pro Glu Cys Lys Arg Ser Arg Phe
            275                 280                 285

(2) INFORMATION FOR SEQ ID NO: 9:
```

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 9:

AAGCTTCCTC AACATCAAAG GGTAGA                                               26

(2) INFORMATION FOR SEQ ID NO: 10:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 10:

AAGCTTCATG ATGAAATCGA TATTGA                                               26

(2) INFORMATION FOR SEQ ID NO: 11:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 11:

GGATCCTCAA TATCGATTTC ATCATG                                               26

(2) INFORMATION FOR SEQ ID NO: 12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 12:

AAGCTTCATT TATGGTTTGA TCCAAC                                               26

(2) INFORMATION FOR SEQ ID NO: 13:

(i) SEQUENCE CHARACTERISTICS:
            (A) LENGTH: 26 base pairs (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 13:

GGATCCGTTG GATCAAACCA TAAATG                                                26

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 14:

GGATCCGTTA ACGTGTGGTC TCGTGT                                                26

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 15:

GAYGARATNG AYWTHGARTT                                                       20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 16:

GTNGGRTCRA ACCANARRTG                                                       20

(2) INFORMATION FOR SEQ ID NO: 17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 17:

CGATGCAGCT GGAATTTCA                                                    19

(2) INFORMATION FOR SEQ ID NO: 18:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 18:

AGTTTGAGCT GCATATCGAA                                                   20

(2) INFORMATION FOR SEQ ID NO: 19:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 19:

TTTGATCCCA CCTCGCCGTT                                                   20

(2) INFORMATION FOR SEQ ID NO: 20:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 20:

CAGCTGACCA AACACAAGCA                                                   20

(2) INFORMATION FOR SEQ ID NO: 21:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 21:

ATTAACCCTC ACTAAAGGGA                                                           20

(2) INFORMATION FOR SEQ ID NO: 22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 22:

TAATACGACT CACTATAGGG                                                           20

(2) INFORMATION FOR SEQ ID NO: 23:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 23:

GTTTTCCCAG TCACGACGT                                                            19

(2) INFORMATION FOR SEQ ID NO: 24:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 24:

AATATCAGCG GAAACAGGG                                                            19

(2) INFORMATION FOR SEQ ID NO: 25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 25:

CCCTGTTTCC GCTGATAATT                                                    20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 26:

CTATTAGCAT CTGCACAGTA                                                    20

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 27:

TACTGTGCAG ATGCTAATAG                                                    20

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 28:

GGAGGACGGG TGAAGACAGA                                                    20

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 29:

```
GTGTAAGGTA GTCCTGATGA                                                        20
```

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 30:

```
TCATCAGGAC TACCTTACAC                                                        20
```

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 31:

```
CCCTTGGATC CGCTATAATT                                                        20
```

(2) INFORMATION FOR SEQ ID NO: 32:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (iii) HYPOTHETICAL: NO (iii) ANTI-SENSE: NO (v) FRAGMENT TYPE: N-terminal (xi) SEQUENCE DESCRIPTION: SEQ ID NO: 32:

```
Met Arg Gly Ser His His His His His His Gly Ser Ala Asp Asn Phe
1               5                   10                  15
Tyr Gln Asp Ala
            20
```

(2) INFORMATION FOR SEQ ID NO: 33:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (iii) HYPOTHETICAL: NO (iii) ANTI-SENSE: NO (v) FRAGMENT TYPE: N-terminal (xi) SEQUENCE DESCRIPTION: SEQ ID NO: 33:

Gly Tyr Pro Arg Arg Pro Val Asp Val Pro Phe Trp Lys Asn Tyr
1               5                   10                  15

(2) INFORMATION FOR SEQ ID NO: 34:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 34:

ATCGGGAGCG GCGATACCGT A                                              21

(2) INFORMATION FOR SEQ ID NO: 35:

(i) SEQUENCE CHARACTERISTICS:
              (A) LENGTH: 7 amino acids
              (B) TYPE: amino acid
              (D) TOPOLOGY: unknown (xi) SEQUENCE DESCRIPTION: SEQ ID NO: 35:

Pro Asn His Asn Arg Val Asp
1               5

(2) INFORMATION FOR SEQ ID NO: 36:

(i) SEQUENCE CHARACTERISTICS:
              (A) LENGTH: 7 amino acids
              (B) TYPE: amino acid
              (D) TOPOLOGY: unknown (xi) SEQUENCE DESCRIPTION: SEQ ID NO: 36:

His Asp Glu Ile Asp Ile Glu
1               5

(2) INFORMATION FOR SEQ ID NO: 37:

(i) SEQUENCE CHARACTERISTICS:
              (A) LENGTH: 7 amino acids
              (B) TYPE: amino acid
              (D) TOPOLOGY: unknown (xi) SEQUENCE DESCRIPTION: SEQ ID NO: 37:

His Leu Trp Phe Asp Pro Thr
1               5

(2) INFORMATION FOR SEQ ID NO: 38:

(i) SEQUENCE CHARACTERISTICS:
              (A) LENGTH: 7 amino acids
              (B) TYPE: amino acid
              (D) TOPOLOGY: unknown (xi) SEQUENCE DESCRIPTION: SEQ ID NO: 38:

Thr Arg Asp His Thr Leu Thr
1               5

(2) INFORMATION FOR SEQ ID NO: 39:

```
        (i) SEQUENCE CHARACTERISTICS:
             (A) LENGTH: 9 amino acids
             (B) TYPE: amino acid
             (D) TOPOLOGY: unknown (xi) SEQUENCE DESCRIPTION: SEQ ID NO: 39:

Asp Glu Ile Asp Xaa Glu Phe Leu Gly
 1               5

(2) INFORMATION FOR SEQ ID NO: 40:

(i) SEQUENCE CHARACTERISTICS:
             (A) LENGTH: 41 amino acids
             (B) TYPE: amino acid
             (D) TOPOLOGY: unknown (xi) SEQUENCE DESCRIPTION: SEQ ID NO: 40:

Asp Glu Met Asp Leu Glu Phe Leu Gly Asn Leu Ser Gly Asp Pro Tyr
 1               5                  10                  15

Thr Leu His Thr Asn Val Phe Ser Gln Gly Lys Gly Asn Arg Glu Gln
            20                  25                  30

Gln Phe His Leu Trp Phe Asp Pro Thr
        35                  40

(2) INFORMATION FOR SEQ ID NO: 41:

(i) SEQUENCE CHARACTERISTICS:
             (A) LENGTH: 41 amino acids
             (B) TYPE: amino acid
             (D) TOPOLOGY: unknown (xi) SEQUENCE DESCRIPTION: SEQ ID NO: 41:

Asp Glu Ile Asp Phe Glu Phe Leu Gly Asn Val Ser Gly Gln Pro Tyr
 1               5                  10                  15

Thr Ile His Thr Asn Val Tyr Thr Gln Gly Lys Gly Asn Lys Glu Gln
            20                  25                  30

Gln Phe His Leu Trp Phe Asp Pro Thr
        35                  40

(2) INFORMATION FOR SEQ ID NO: 42:

(i) SEQUENCE CHARACTERISTICS:
             (A) LENGTH: 41 amino acids
             (B) TYPE: amino acid
             (D) TOPOLOGY: unknown (xi) SEQUENCE DESCRIPTION: SEQ ID NO: 42:

Asp Glu Ile Asp Phe Glu Phe Leu Gly Asn Met Ser Gly Asp Pro Tyr
 1               5                  10                  15

Thr Leu His Thr Asn Val Tyr Thr Gln Gly Lys Gly Asp Lys Glu Gln
            20                  25                  30

Gln Phe His Leu Trp Phe Asp Pro Thr
        35                  40

(2) INFORMATION FOR SEQ ID NO: 43:

(i) SEQUENCE CHARACTERISTICS:
             (A) LENGTH: 46 amino acids
             (B) TYPE: amino acid
             (D) TOPOLOGY: unknown (xi) SEQUENCE DESCRIPTION: SEQ ID NO: 43:

Asp Glu Ile Asp Ile Glu Phe Leu Gly Thr Ile Pro Gly Lys Pro Tyr
```

-continued

```
1               5              10              15
Thr Leu Gln Thr Asn Val Phe Ile Glu Gly Ser Gly Asp Tyr Asn Ile
            20                  25              30

Ile Gly Arg Glu Leu Arg Ile His Leu Trp Phe Asp Pro Thr
            35              40              45
```

US 6,215,044 B1

TOMATO XYLOGLUCAN ENDO-TRANSGLYCOSYLASE NUCLEIC ACIDS

FIELD OF THE INVENTION

This invention relates to nucleotide sequences encoding a plant enzyme, vectors containing said nucleotide sequences, hosts containing said nucleotide sequences, amino acid sequences encoded by said nucleotide sequences, recombinant DNA methods of producing the enzyme, and a method of altering the properties of a plant.

BACKGROUND OF THE INVENTION

Fruit and vegetable cell walls are largely polysaccharide, the major components being pectin, cellulose and xylogucan (Selvendran & Robertson, IFR Report 1989). Numerous cell wall models have been proposed which attempt to incorporate the essential properties of strength and flexibility (e.g. Albersheim, 1975 Sci. Am. 232, 81–95; Albersheim, 1976 "The primary cell wall", Plant Biochemistry, 3rd Edition, Academic Press; and Hayashi, 1989, Ann. Rev. Plant Physiol. & Plant Mol. Biol. 40, 139–168).

Xyloglucans are 1,4-β-glucans that are extensively substituted with α-1,6-xylosyl side chains, some of which are 1,2 β-galactosylated. They are found in large amounts in the primary cell walls of dicots but also in certain seeds, where they serve different roles.

Primary cell wall xyloglucan is tightly hydrogen bonded to cellulose microfibrils and requires concentrated alkali or strong swelling agents to release it. Xyloglucan is thought to form cross-bridges between cellulose microfibrils, the cellulose/xyloglucan network forming the major load-bearing/elastic network of the wall. DCB mutated suspension culture cells (cell walls lacking cellulose) release xyloglucan into their media, suggesting that xyloglucan is normally tightly bound to cellulose.

Hydrolysis of primary cell wall xyloglucan has been demonstrated in segments of dark grown squash hypocotyls, during IAA induced growth (Wakabayashi et al., 1991 Plant Physiol. 95. 1070–1076). Endohydrolysis of wall xyloglucan is thought to contribute to the wall loosening which accompanies cell expansion (Hayashi, cited previously). The average molecular weight of xyloglucan has also been shown to decrease during tomato fruit ripening and this may contribute to the tissue softening which accompanies the ripening process (Huber, 1983 J. Amer. Soc. Hort. Sci. 108, 405–409).

Certain seeds, e.g. nasturtium, contain up to 30% by weight of xyloglucan, stored in thickened cotyledonary cell walls, which serves as a reserve polysaccharide and is rapidly depolymerised during germination.

An endo 1,4 β-D glucanase which specifically acts on xyloglucan (i.e. a xyloglucanase) has been isolated and purified to apparent homogeneity from germinating nasturtium (*Tropaeolum majus* L.) seeds (Edwards et al., 1986 J. Biol. Chem. 261, 9494).

The purified xyloglucanase gives a single polypeptide band on SDS polyacrylamide gel electrophoresis, (apparent molecular weight, 29–31 kDa) and isoelectric focusing (isoelectric point, 5.0). The enzyme displays an absolute specificity for xyloglucan and an endo mode of action, as determined by end product analysis following hydrolysis of tamarind seed xyloglucan (Wakabayashi et al., cited above). Although the natural substrate of the enzyme is nasturtium cotyledonary reserve xyloglucan, it has also been shown to hydrolyse primary cell wall xyloglucans in vitro (Edwards et al., cited previously). At high substrate concentrations, xyloglucan endo-transglycosylase (XET) activity has been demonstrated (Fanutti et al., 1993 The Plant Journal 3, 691–700).

The nucleotide sequence of this nasturtium xyloglucanase/XET enzyme has been determined and is disclosed in International Patent Application No. WO 93/17101 and by de Silva et al., (1993 The Plant Journal 3, 701–711).

Similar enzyme activity has been detected in other plant tissue and shown to be positively correlated with growth rate in different zones of the pea stem (Fry et al., 1992 Biochem. J. 282, 821–829). It has been proposed that XET is responsible for cutting and rejoining intermicrofibrillar xyloglucan chains and that this causes the wall-loosening required for plant cell expansion. XET activity has also been demonstrated in tomato fruit (xyloglucanase apparently activatable by xyloglucan oligosaccharides) where it is reportedly highest at the 2 days post-"breaker" stage of ripening (Machlachlan & Brady, 1992 Aust. J. Plant Physiol. 19, 137–146) and may be involved in the softening process.

This application describes the isolation from tomato plants of a nucleotide sequence which encodes an XET activity.

SUMMARY OF THE INVENTION

In a first aspect the invention provides a polypeptide having xyloglucan endo-transglycosylase (XET) activity, comprising substantially residues 21–289 of the amino acid sequence of FIG. 1 (Seq ID No. 2), or functional equivalents thereof.

The term "functional equivalent" as used herein and applied to an amino acid sequence is intended to refer to those amino acid sequences having the same functional characteristics as the sequence of the invention but which have slightly different sequences. Generally, for example, it is well known that one may make a "conservative" substitution, exchanging one amino acid residue in a sequence for another residue with very similar properties, without having any significant effect on the function of the polypeptide.

An example of a functionally equivalent polypeptide sequence is shown in FIG. 5 (Seq ID No. 8). The amino acid sequences shown in FIGS. 1 and 5 are directly compared in FIG. 6.

Further, one or more amino acid residues may be deleted or added without significant deleterious effect. It will be apparent to those skilled in the art that such changes may particularly be made at points in the sequence which are not evolutionarily conserved. Enzyme precursors are also included within the meaning of "functional equivalents" and also mature, processed enzymes lacking signal sequences. In the present case amino acid residues 1–20 of FIG. 1 are believed to constitute such a signal sequence and are therefore not essential for enzyme activity. Likewise, amino acid residues 1–18 of the sequence shown in FIG. 5 are thought to comprise a non-essential signal sequence.

In specific embodiments therefore the invention may provide a polypepide having XET activity and comprising residues 1–289 of the sequence shown in FIG. 1; or residues 19–287 of the amino acid sequences shown in FIG. 5; or residues 1–287 of the amino acid sequence shown in FIG. 5.

Preferably such functional equivalents will exhibit at least 80% homology, and more preferably at least 85% homology, and most preferably at least 90% homology, with the amino acid sequence of the invention.

The present inventors have, by analysis of the amino acid sequence data, identified a number of peptide sequences which are thought to be relatively conserved within functional equivalents of the sequence of the invention.

Preferably, functional equivalents will comprise substantially one or more of the following peptide sequences (which will generally be perfectly conserved but may contain up to one or, at most, two amino acid differences):

DEIDFEFLGN; SLWNADDWAT; FYSKNEYLFG; and GTVTTFYLSS; (Seq ID Nos. 3–6 respectively).

Desirably the polypeptide is substantially in isolation from other plant derived substances.

In a second aspect the invention provides a nucleotide sequence encoding the amino acid sequence of FIG. 1 (Seq ID No. 1), or functional equivalents thereof.

Preferably the nucleotide sequence comprises the nucleotide sequence of FIG. 1 or other functionally equivalent sequences obtainable from tomato plants. The term "functional equivalent" as used herein and applied to nucleotide sequences is intended to refer to nucleotide sequences encoding a polypeptide having the same functional characteristics as the amino acid sequences of the first aspect and includes nucleotide sequences which will hybridize under standard conditions (described by Sambrook et al. 1989, Molecular Cloning: A Laboratory Manual) to the complement of the nucleotide sequence of FIG. 1. Preferably the functionally equivalent nucleotide sequence will exhibit at least 70% homology, more preferably 80% homology and most preferably at least 85% homology with the nucleotide sequence of FIG. 1. A specific example of a functionally equivalent nucleotide sequence is shown in FIG. 5 (Seq ID No. 7).

For the purposes of the present specification, the term "functional equivalent" also refers to "anti-sense" sequences which hybridise under standard conditions to the nucleotide sequence of FIG. 1. Such sequences have utility in downregulating the expression of the nucleotide sequence of the invention. Preferably such anti-sense functional equivalents will exhibit at least 70% homology, more preferably at least 80% homology, and most preferably at least 90% homology with the complement of the nucleotide sequence of FIG. 1. In general, anti-sense functional equivalents will preferably exhibit higher percentage homology than sense equivalents. This is because sense constructs will be translated into polypeptides which will be functional and which may contain conservative amino acid substitutions. In contrast, antisense constructs will, in the vast majority of instances, function at the level of nucleic acid rather than polypeptide, and thus any base sequence differences will tend to reduce the usefulness of the construct.

Those skilled in the art will understand that, with the benefit of the disclosure herein relating to the nucleotide and amino acid sequences of the invention, it will be simple to detect, isolate and clone (e.g. by PCR) other nucleotide sequences which are functionally equivalent to the nucleotide sequence of the invention. Suitable methods, for example, are taught by Sambrook et al. Of particular usefulness in such routine work may be the peptide sequences disclosed above. Also, the polypeptide of the invention (or peptides derived therefrom) may be used to generate antibodies for use in immunological screening of putative functionally equivalent sequences.

It is preferred that the sequence of the second aspect of the invention further comprises a 5' untranslated region including a suitable promoter, to enable expression in host cells.

The invention also provides a vector comprising the nucleotide sequence of the second aspect of the invention, and a host cell comprising the nucleotide sequence of the invention.

In one embodiment, the vector is capable of expressing the nucleotide sequence, so as to produce the polypeptide of the invention. (Other vectors may comprise an antisense functionally equivalent nucleotide sequence).

Thus, in a further aspect, the invention provides a method of producing a polypeptide having XET activity, comprising the steps of: introducing into a suitable host cell a vector capable of directing the expression of a polypeptide as defined above, growing the host cell and/or the progeny thereof in suitable culture conditions so that the polypeptide is expressed, followed by obtaining the polypeptide from either the culture medium and/or the host cells.

It is preferable, but by no means essential, that the host cell is eukaryotic, as a eukaryotic host is more likely to express the enzyme in a fully functional conformation.

Suitable vectors are known which can be used to introduce and express the sequence of the invention in plants.

In a further aspect the invention provides a method of transforming a host cell, comprising the introduction into the host cell of the nucleotide sequence of the second aspect of the invention. Preferably the host cell is a plant cell. Preferably the transformed plant cell comprises part of a plant.

As will be apparent to those skilled in the art, the introduction of the nucleotide sequence of the invention into a plant or part thereof would be expected to alter the characteristics of the plant or part thereof.

In a still further aspect, the invention provides a method of altering the characteristics of a plant or part thereof, comprising introducing into the plant or part thereof an effective portion of the nucleotide sequence of the invention or a functional equivalent thereof, so as to alter the level of XET activity in the plant or part thereof. Preferably the method is such as to reduce the level of XET activity in the plant or part thereof, typically by introducing an antisense sequence. Preferably the effective portion will comprise at least 50%, more preferably at least 70%, and most preferably at least 90% of the nucleotide sequence of the invention?

In another aspect, the invention provides a genetically engineered plant having characteristics altered by the method defined above, or the progeny of such a plant.

The altered plant is preferably any commercially important plant (including fruit or vegetable plants) where there is sufficient knowledge to perform the method of the invention and in which xyloglucan has a structural function (i.e. dicots and non-Grarinaceous monocots).

Such plants include: alfalfa, apple, broccoli, cabbage, carrot, cauliflower, celery, cotton, cranberry, cucumber, eggplant, flax, grape, horseradish, kiwi, lettuce, mangoes, melon, oilseed rape, papaya, pea, peaches, pears, peppers, plum, poplar, potato, raspberry, soybean, spruce, strawberry, sugarbeet, sweet potato, tobacco, tomato and walnut.

It will be appreciated that the characteristics of the whole plant need not be altered. It may be desirable to alter the properties of parts of the plant (e.g. seeds, fruit). This could be achieved, for example, by the use of tissue-specific promoters to regulate transcription of the introduced sequence.

The method of the invention would be expected to alter levels of XET activity and thus the frequency of breaking and re-forming of cell wall cross-links (consisting of xyloalucan molecules) resulting in wall loosening which may permit cell expansion. Moreover, in view of the important structural role of xyloglucan, one might expect the characteristics which might be altered to include: size, rate of growth, and texture, especially during ripening.

BRIEF DESCRIPTION OF THE DRAWINGS

The invention is further described by reference to the following illustrative example and drawings, in which:

FIGS. 1A–1B shows an amino acid and nucleotide sequence (clone B1, Seq ID Nos. 1–2) in accordance with the invention;

FIG. 2 shows partial amino acid sequences (Seq ID Nos. 40–43) of a polypeptide in accordance with the invention and a functional equivalent thereof, compared with two prior art amino acid sequences;

FIGS. 3A–3D show the sequencing strategy used to determine the sequence shown in FIG. 1, (E=EcoRI, P=Pst, H=HindIII) and primers (Seq ID Nos. 17–20) are shown;

FIGS. 4A–4D show the sequencing strategy used to determine the sequence of a nucleotide (clone B2) in accordance with the invention (E=EcoRI, P=Pst) and primers (Seq ID Nos. 24–30) are shown;

FIGS. 5A–5B show a nucleotide sequence (clone B2, Seq. ID Nos. 7–8) and amino acid sequence in accordance with the invention;

FIGS. 6A–6B show a comparison of two functionally equivalent amino acid sequences (dot=identical amino acid; triangle=predicted cleavage site; Seq ID Nos. 1–2 and 8)

DETAILED DESCRIPTION OF THE INVENTION

EXAMPLES

Example 1

Figure 3A:
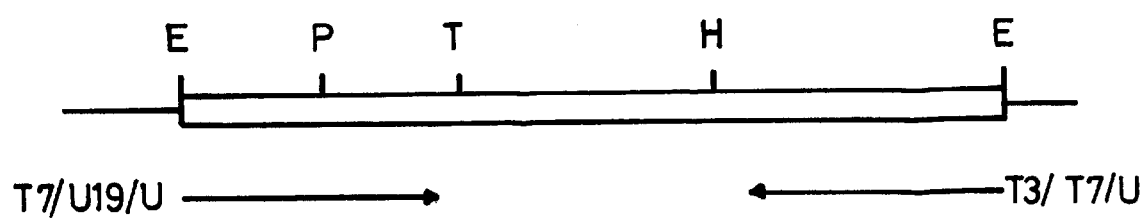

Following complete sequencing of a cDNA encoding nasturtium seed XET (described in pending International Patent Application No. WO 93/17101), primers were designed to attempt PCR amplification of similar gene fragments from tomato. Two of the primers (NXG2H and NXG2B, shown below) overlapped with a region homologous to a *Bacillus macerans* β-1,3-1,4-glucanase (the region having the amino acid sequence DEIDIEFLG). The other primers corresponded to regions adjacent to or surrounding histidine residues; (these are often present in active sites of hydrolytic enzymes, and active sites of enzymes of similar function often having primary sequence homology). These corresponded to amino acid sequences PNHNRVD (primer NXG1H), HDEIDIE (primers NXGH2H and NXG2B), HLWFDPT (primers NXG3H and NXG3B) and TRDHTLT (primer NXG4B) (Seq ID Nos. 35–38, respectively).

```
              (Seq ID Nos. 9-14, respectively)
NXG1H  5'  AAGCTTCCTCAACATCAAAGGGTAGA 3'  (sense)

NXG2H      AAGCTTCATGATGAAATCGATATTGA      (sense)

NXG2B      GGATCCTCAATATCGATTTCATCATG      (antisense)

NXG3H      AAGCTTCATTTATGGTTTGATCCAAC      (sense)

NXG3B      GGATCCGTTGGATCAAACCATAAATG      (antisense)

NXG4B      GGATCCGTTAACGTGTGGTCTCGTGT      (antisense)
```

These primers were completely conserved with respect to the nasturtium sequence and incorporated restriction enzyme recognition sites at their 5' ends to facilitate cloning of PCR products. However all attempts to amplify tomato DNA by PCR, using any combination of the above primers, proved unsuccessful.

The deduced amino acid sequence of nasturtium seed XET shares some regions of homology (42% identity in a 151aa overlap) with a sequence deduced from a genomic clone and cDNA from *Arabidopsis thaliana* (Medford et al., 1991 The Plant Cell 3, 359–370). The polypeptide encoded by the genomic clone is termed meri-5 and its function is currently unknown.

It was decided to attempt PCR amplification of tomato DNA using a mixture of degenerate oligonucleotides (XG 117 and XG 162, shown below) corresponding to two of these regions conserved between nasturtium XET and meri-5, although there was little expectation of success in view of the previous failures and the lack of knowledge concerning the function (if any) of meri-5.

Surprisingly, PCR succeeded in amplifying a 122 bp tomato genomic DNA fragment having significant sequence homology to both meri-5 and nasturtium XET.

The experiment was performed as described below.

Genomic DNA was isolated from young tomato leaf tissue (cultivar VF 143B-7879, available from the Tomato Genetics Stock Centre, Department of Vegetable Crops, University of California, Davis, Calif. 95616), as described by Dellaporta et al. (1983, Plant Mol. Biol. 1, 19–21).

The degenerate oligonucleotide mixtures were designed corresponding to the conserved regions DEID(I/F)EFLG (XG 117, Seq. ID No. 39) and HLWFDPT (XG 162, Seq. ID No. 37), as shown below:

XG 117 5' GA(C/T) GA(A/G) ATI GA(C/T) (A/T)T(A/C/T) GA(A/G) TT 3' (sense)

XG 162 3' GT(G/A) (G/A)A(G/A/T/C) ACC AA(G/A) CT(G/A) GGI TG 5' (antisense) (Seq ID Nos. 15 and 16 respectively)

The degenerate oligonucleotides were then used as primers in the following reactions (each reaction having a total reaction volume of 100 μl): 1–2 μg genomic DNA; 100 picomoles each of XG 117 and XG 162; dGTP, dATP, dTTP and dCTP all at 0.2 mM; 10 mM Tris-HCl pH 8.3; 50 mM KCl; 1.5 mM MgCl$_2$; 0.01% (W/V) gelatin; and 2.5 units Taq DNA polymerase (Stratagene).

Thermal cycling was carried out in an MJ Research programmable thermal controller with an initial denaturing step of 94° C. for 2 minutes, followed by 35 cycles of 94° C. for 1 minute, 40° C. for 2 minutes and 72° C. for 2 minutes. Amplification products were fractionated on a 2% agarose/TBE gel containing 0.5 μg/ml ethidium bromide and viewed on a UV transilluminator. DNA fragments were purified from gels using DEAE paper, as described by Sambrook et al. (Molecular Cloning: a laboratory Manual).

The main PCR product was found to be 122 bp in size. This was ligated into pT7Blue (obtained from AMS Biotechnology) and subjected to DNA sequence analysis. Of the four clones sequenced, three had identical DNA sequences (PX3) and one differed in both DNA and deduced amino acid sequence (PX1), as shown in FIG. 2. In FIG. 2, Tom 3 and Tom 1 represent the deduced amino acid sequence for PX3 and PX1 respectively, as compared with Meri-5 and nasturtium XET.

In order to obtain more extensive sequence information, a tomato cDNA 5' stretch library was obtained from Clontech Laboratories Inc. (prepared using mRNA from the "breaker" stage of ripening fruit from tomato, "Ailsa craig" cultivar VFN8); this was primed with oligo-(dT) and random primers to synthesise cDNA, which was packaged in phage lambda gt11.

Approximately 200,000 cDNA clones from this library were screened using the 122 bp PCR fragment as a radiolabelled probe. Briefly, 25–30 ng of gel-purified 122 bp amplification product were denatured in 9 μl H$_2$O by heating at 100° C. for 5 minutes and then cooling on ice. The fragments were radio-labelled with $^{32}$P-dCTP (Amersham International plc) using a kit supplied by United States Biochemicals Inc. (Sequenase v2.0). Unincorporated nucleotides were removed by chromatography through a Sephadex G-50 column.

Using this probe, a number of positively-reacting clones were detected in the cDNA library. These were eluted from top layer agarose into 0.1-1ml SM (50 mM Tris-HCl pH 7.5, 10 mM MgSO$_4$, 100 mM NaCl, 0.01% w/v gelatin) and purified by further rounds of screening. The insert was isolated from the bacteriophage either by direct PCR of the stock suspension or by digestion of isolated DNA.

For PCR of the stock suspension, purified bacteriophage stocks (5 μl, 10$^5$–10$^6$pfu) were heated at 100° C. for 5 minutes and added to a solution identical to that described previously except that 20 pmols each of gtll 5' and 3' oligonucleotides (Clontech) were used instead of the degenerate ones. Thermal cycling was as follows: 2 minutes at 94° C., 25 cycles of 1 minute at 94° C., 1 minute at 55° C. and 2 minutes at 72° C., followed by a final step of 5 minutes at 72° C. Amplification products were gel-purified on 1% agarose gels as above.

Gel-purified PCR-amplified products were ligated into pT7 Blue PCR cloning vector (AMS Biotechnology Limited) and transformed into competent E. coli according to the manufacturer's instructions.

Colonies containing recombinant plasmids were used to inoculate 30 ml Lennox broth containing 50 μg/ml ampicillin and 12.5 μg/ml tetracycline; after overnight growth at 37° C., purified plasmid DNA was obtained from the culture using a "Plasmid midi" kit supplied by Qiagen Inc. Restriction analysis of the cloned products was carried out using enzymes and buffers supplied by Amersham International plc, followed by agarose gel electrophoresis.

DNA was sequenced using kits and protocols supplied by United States Biochemicals Inc. (Sequenase v2.0). Recombinant plasmids (Qiagen-prepared) were either sequenced directly or restriction fragments were subcloned into M13 to produce single-stranded templates. Reaction products were fractionated on 30 cm×40 cm×0.4 mm polyacrylamide gels using BRL 6% acrylamide solutions. An IBM computer with DNAstar software was used to analyse resultant sequences.

Figure 3B:
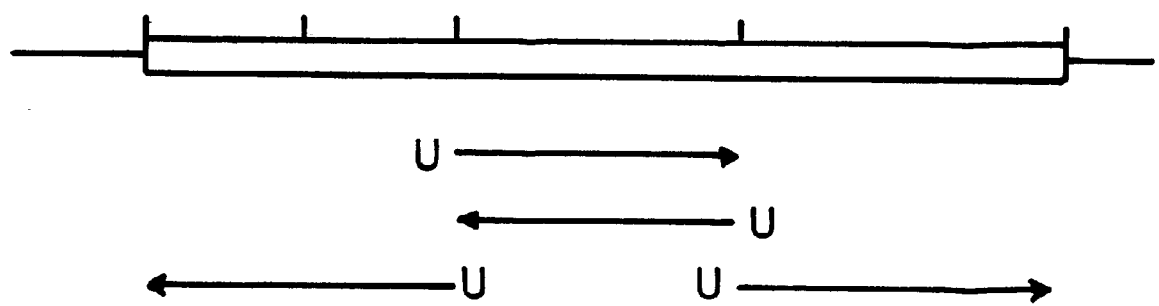
Figure 3C:
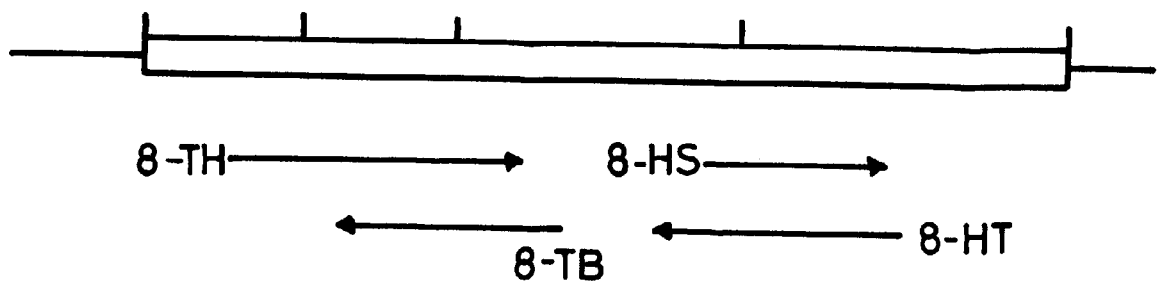

Clones were found to vary in size between 500 and 1400 bp. One clone, termed clone tXET-B1 (or "B1" for simplicity), was found to possess internal HindIII and SacI recognition sites which facilitated subcloning into M13. Internal primers were also used in order to sequence the clone fully and in both directions (FIG. 3). The sequences of these internal primers (8-TH, 8-HS sense primers and 8-TB, 8-HT antisense primers) are as follows:

8-TH: 5' CGATGCAGCTGGAATTTCA 3'
8-TB: 5' AGTTTGAGCTGCATATCGAA 3'
8-HS: 5' TTTGATCCCACCTCGCCGTT 3'
8-HT: 5' CAGCTGACCAAACACAAGCA 3'

(Seq ID Nos. 17–20 respectively)

The sequences of the other primers were:

T3: 5' ATTAACCCTCACTAAAGGGA 3'
T7: 5' TAATACGACTCACTATAGGG 3'
U19: 5' GTTTTCCCAGTCACGACGT 3'

(Seq ID Nos. 21–23 respectively)

U represents the M13 (-40) primer. Initially, two sequences were found, each from a different PCR amplification from the lambda stock. They differed in 2 base pairs within the putative coding region. Since these differences were probably due to the inaccuracy of the thermostable DNA polymerase used in the PCRs, lambda DNA was prepared and the cDNA ligated into pBluescript SK+, in order to obtain definitive sequence data (FIG. 1). The definitive nucleotide sequence of clone B1 is shown in FIG. 1, together with the deduced amino acid sequence.

The putative open reading frame of clone B1 encodes a 289 amino acid polypeptide of predicted molecular weight 32.7 kDa. This has 39% identity in 270 overlapping amino acids with nasturtium XET and 59% identity in an overlap of 186 amino acids with meri-5.

A signal peptide is predicted on the basis of hydrophobicity of amino acids in positions 1–25, and statistical analysis of the amino acid sequence predicted that the precursor is cleaved between alanine and aspartate residues at positions 20 and 21 (Von Heijne, 1983 Eur. J. Biochem. 113, 17–21).

The region of clone B1 corresponding to the genomic PCR fragments (aa 103–129) shows differences in the deduced amino acid sequence compared to both of the genomic fragment sequences. This suggests that clone B1 is part of a multi-gene family in tomato. A putative N-glycosylation site (Asn-X-Ser/Thr; aa 105–107) was identified, which is also present in meri-5 and the genomic fragments, but not nasturtium XET.

Figure 4A:
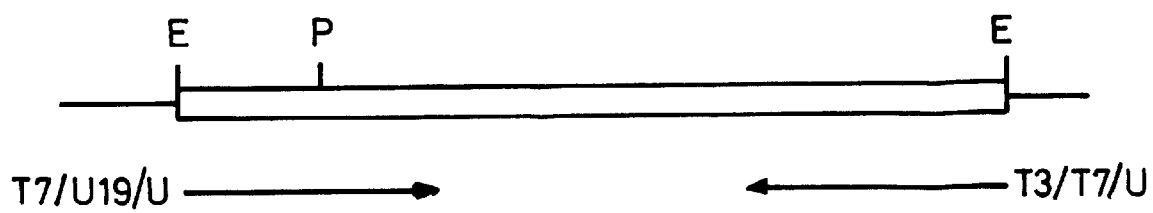
Figure 4B:
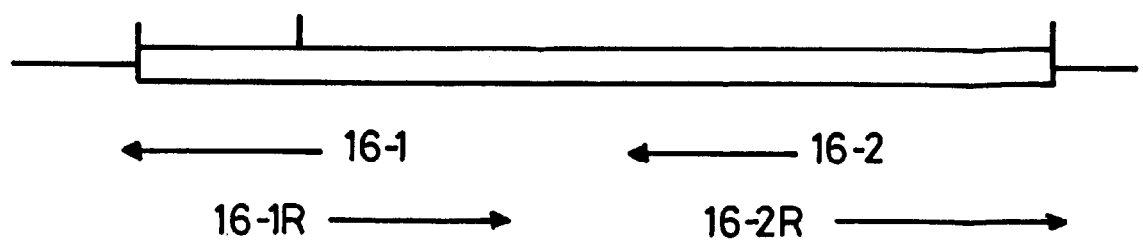
Figure 4C:
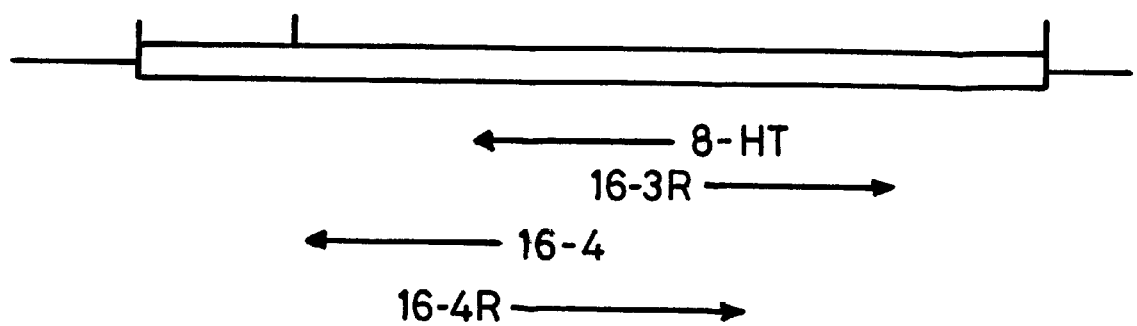

The second clone obtained, termed clone tXET-B2 (abbreviated to "B2"), was larger than clone B1 but had no convenient restriction sites for subcloning, so several internal primers were used to complete DNA sequencing. The strategy used to determine the sequence of clone B2 is shown schematically in FIG. 4. In FIG. 4. E=EcoRI site, P=PstI site; (a) shows sequencing using vector primers, (b) and (c) shows sequencing with internal primers. A number of primers were employed, including:

16-1: 5' AATATCAGCGGAAACAGGG 3'
16-1R: 5' CCCTGTTTCCGCTGATAAT 3'
16-2: 5' CTATTAGCATCTGCACAGTA 3'
16-2R: 5' TACTGTGCAGATGCTAATAG 3'
16-3R: 5' GGAGGACGGGTGAAGACAGA 3'
16-4: 5' GTGTAAGGTAGTCCTGATGA 3'
16-4R: 5' TCATCAGGACTACCTTACAC 3'

(Seq ID Nos. 24–30 respectively)

A deduced open reading frame of 287 amino acids was identified. The determined nucleotide sequence and deduced amino acid sequence of clone B2 are shown in FIG. 5. FIG. 6 shows the cDNA sequence of clone B1 and deduced amino acid sequence thereof, in direct comparison with the deduced amino acid sequence for clone B2. (In FIG. 6, dots indicate identical amino acids, and the arrow indicates the predicted signal peptide cleavage site.) The predicted signal peptide for clone B2 was 2 amino acids shorter than that of clone B1, leaving a mature polypeptide of 269 amino acids. A putative N-glycosylation site was found in the same position as for clone B1. Sixteen amino acid differences between the predicted mature polypeptides of clones 8 and 16 were identified, 14 of which were conservative.

Hydrophobic Cluster Analysis (HCA, as described by Gaboriaud et al., 1987 FEBS Letters 224, 149–155 and Henrissat et al., 1988 Biochem. J. 255, 901–905) was performed to investigate possible conformational homology of the polypeptide encoded by clone B1 with other known proteins.

HCA plots were produced from the deduced amino acid sequences of nasturtium XET, meri-5 and tomato clone B1 using WordPerfect™ 5.1 macros, using a modified 2D representation of an α-helix (Henrissat et al. cited above). Hydrophobic clusters were encircled by hand, aligned manually and HCA homology scores calculated.

Similar folding was predicted for all three proteins on the basis of (a) "continuous presence of conserved clusters" throughout most of the length of the sequence and (b) overall HCA homology scores for all three comparisons being more than 75% (meri-5 v. tomato XET clone B1, 86%; nasturtium XET v. tomato XET clone B1, 80%; meri-5 v. nasturtium XET, 78%).

This supports data from primary sequence homology and secondary structure predictions (Kyte & Doolittle 1982, J Mol Biol 157, 105–132) which suggest that these three proteins are likely to have broadly similar folding and therefore similar function, whilst differing in detail.

It was decided to attempt to express clone B2 in *E. coli*. This is described below in Example 2.

Example 2

Manipulation of Clone B2 for Expression in *E. coli*

A BamHI recognition sequence was introduced close to the N-terminal coding sequence of the putative mature protein by PCR, using a mutagenic primer (16-1 B: CCCTT GGATCCGCTATAATT Seq ID No. 31) and a pBluescript primer (T3; Stratagene). Reaction conditions were: 1 ng XET clone B2 in pBluescript SK+, 0.4 mM each of dATP, dCTP, dGTP and dTTP, 25 pmols of each primer, 1×VENT polymerase buffer and 0.25 units VENT DNA polymerase (New England Biolabs Inc.). Thermal cycling was 2 minutes at 93° C., 25 cycles of 1 minute at 93° C., 30 seconds at 55° C. and 1 minute at 72° C.

Over-expression of Recombinant Tomato XET in *E. coli*

Expression of tomato XET in *E. coli* was achieved using the QIAGEN QIAexpress™ system. A BamHI-HindIII fragment of the mutagenised PCR product was ligated into the expression vector pQE30 and transformed into *E. coli* M15 cells containing the pREP4 repression plasmid. The expression vector allows incorporation of a 6×histidine tagged N-terminal which has high affinity for Ni-NTA (Ni-NTA is nickel-nitrilo tri-acetic acid) resin provided by QIAGEN. Cells were grown in Lennox broth containing appropriate antibiotics and induced with 2 mM IPTG when the optical density of the culture at 600 nm was 0.7–0.8. Growth was then allowed to continue for 3–5 hours. For analysis, cells were pelleted from 0.5 ml of the culture, boiled in sample buffer (Laemmli 1970 Nature 227, 680–685) and run on SDS-polyacrylamide gels (10%); separated proteins were stained in Coomassie blue. Localisation of tagged proteins was established as in protocol 4 of "The QIAexpressionist" 2nd edition (1992; QIAGEN Inc.).

Recombinant Tomato XET Protein Purification and Refolding

Recombinant tomato XET was purified under denaturing conditions on Ni-NTA resin as described in "The QIAexpressionist" protocol 7, except that after the final wash, the column with bound protein was equilibrated in 6M urea, 0.5M NaCl, 20% glycerol, 40 mM Tris-HCl pH7.4. An FPLC-mediated 6M-1M urea gradient (24 ml at a rate of 0.25 ml/min) in the above solution was then used to refold the bound protein, which was eluted in 10 ml 1M urea, 0.5M NaCl, 20% glycerol, 40 mM Tris-HCl pH7.4, 250 mM imidazole.

Assays for XET Activity $^3$H-labelled XG oligosaccharides were obtained from S C Fry, (University of Edinburgh) and their incorporation into polymeric XG assayed as described by Fry et al. (1992 Biochem. J. 261, 9489–9494). Protein concentration was estimated using a kit supplied by BioRad.

N-terminal Amino Acid Sequencing

Purified recombinant proteins were subjected to electrophoresis as above, using high quality reagents. They were then electroblotted (0.5 A, 2 hours) onto Problott™ membrane (a derivatised PVDF material, obtained from ABI) and stained in 1% Coomassie Brilliant Blue, 50% methanol. The blotted protein was subjected to sequential Edman degradation on an ABI gas phase sequencer model 740, with pulse liquid update, as described by Cottingham et al. (1988 Biochim. Biophys. Acta 956, 201–207).

Expression and Characterisation of Recombinant Tomato XET

Tomato XET was expressed in *E. coli* with an N-terminal 6×His tag to facilitate purification. A tagged protein of the predicted molecular weight (32 kDa) was found in the insoluble fraction; phase contrast microscopy of the expressing culture showed strongly refracting bodies in each cell, suggesting the presence of insoluble inclusion bodies (data not shown). Following large-scale purification under denaturing conditions, the tagged protein was subjected to N-terminal amino acid sequencing. The resulting sequence (MRGSHHHHHHGSADNFYQDA Seq ID No. 32) confirmed both the identity of the protein as recombinant tomato XET, and the presence of the N-terminal 6×His tag.

Recombinant tomato XET was refolded whilst bound to the Ni-NTA agarose resin, by a reverse urea gradient. Following elution from the column, 15 μl was assayed for incorporation of $^3$H-XG oligosaccharides (XGOs) into polymeric XG: approximately 400 Bq of $^3$H-XGOs were incorporated per kBq provided, per hour, per μg protein. Following dialysis against 0.5M NaCl, 50 mM Tris-HCl pH7.2, 20% glycerol, specific activity increased to approximately 700 Bq/kBq hour μg.

Clone B2 was thus over-expressed in *E. coli* with the apparent N-terminal signal peptide replaced with a 6×histidine tag which facilitated purification. Following purification and refolding, the recombinant protein was able to catalyse incorporation of radiolabelled XG oligosaccharides into polymeric XG, confirming it as an XET. The specific activity of the refolded XET is relatively low; a crude stem extract from a growing tomato plant has an XET specific activity of about 100 Bq/kBq hour μg, compared to 700 Bq/kBq μg for refolded XET. Since the recombinant protein is greater than 90% pure, this is presumably due to most of the protein not being correctly refolded.

Unlike nasturtium seed XET, a putative N-glycosylation site is present in both clones' amino acid sequences. It is interesting to note that, recombinant expression in *E. coli*, which does not glycosylate proteins, resulted in active XET. This shows that the glycosylation is not necessary for XET activity in vitro, raising questions about its role in vivo. The lack of glycosylation in nasturtium seed XET may reflect its specialist role in storage reserve mobilization.

Evidence for the function of XET in plants is rapidly accumulating. The hypothesis that XET plays a role in plant growth is supported by its correlation with growth along the length of pea stems (Fry et al, 1992 Biochem. J. 282, 821–828) and in maize roots (Pritchard et al, 1993 J. Exp. Bot. 44, 1281–1289). It is thought to act by loosening the cell wall to permit cell expansion.

XET is also likely to be involved in fruit ripening, as suggested by its changing levels in fruits as diverse as tomato, pear (unpublished observations of the inventors) and kiwi (Fry 1993 Current Biology, 3 (no. 6), 355–357). Here XET may improve access of other enzymes to the tightly packed networks of the cell wall. This would be supported by the small, compact nature of XET (Edwards et al., 1986 J. Biol. Chem. 261, 9489–9494). Alternatively, XET may be involved (possibly in conjunction with other cell wall hydrolases) in the depolymerisation of xyloglucan which occurs during fruit ripening.

Example 3

In addition to the recombinant DNA work described above, attempts were made to isolate and purify a polypeptide having XET activity from tomato plants.

Step 1: Assay for Activity of XET

XET activity in various crude tomato fruit extracts was measured by incorporation of $^3$H-labelled xyloglucan oligosaccharides into xyloglucan polymer. This assay measures transglycosylase activity. Each assay contained the following components: 10 μl 0.2M Na-Mes, pH 6.0 (Na-Mes is Na 2-[N-Morpholino] ethanesulphonic acid), 10 μl 8 mg/ml xyloglucan, and 5 μl [$^3$H] XGO (0.7 KBq).

Assays were incubated at 25° C. for 1 hour, and stopped by addition of 100 μl 20% formic acid. The assay mixture was then spotted onto a 5×5 cm disc of cellulose filter paper (Whatman 3MM Chromatography paper). It has been established that xyloglucan polymer (whether labelled or unlabelled with [$^3$H]XGO) will bind to the cellulose filter, whereas [$^3$H]XGO oligosaccharides will not. The filters were allowed to dry and unincorporated [$^3$H]XGO was removed by washing under running tap water for 30 min. The filters were dried again at 60° C., then rolled, loaded face outwards, into a cylinder and placed in a 22 ml scintillation vial. Scintillant (2 ml of Betamax ES) was added and the filters counted for $^3$H. This assay is essentially as described by Fry et al. (1992), cited above.

Step 2: Extraction of XET from Tomato Pericarp

A variety of extraction buffers were used and their effectiveness assessed. It was found that XET was efficiently extracted by 0.1 M sodium phosphate buffer, pH 7.2. It was also found that retention of XET activity was highly dependent on ionic strength, and activity was lost if the ionic strength of chromatography buffer etc. was less than 0.2M.

Step 3: Choice of Starting Material for Purification

Crude extracts were made (in 0.1 M sodium phosphate buffer, pH 7.2) from tomato pericarp (*Lycopersicum esculentum*, var. Moneymaker) tissues taken from all stages of growth and ripening. It was consistently found (from several experiments) that small green fruit (i.e. less than 35 mm in diameter) had the highest XET activity, whether expressed as total or specific activity. Therefore the pericarp of small green fruit was used as the starting material for purification.

Step 4: Ammonium Sulphate Precipitation

Pericarp tissue (100 g) from small green fruit of less than 35 mm in diameter was harvested, frozen in liquid nitrogen, and stored at −20° C. or −70° C.. The tissue was homogenised in 1 g:1.5 vol 0.1 M sodium phosphate, pH 7.2 with 1.0% (w/v) insoluble PVP (polyvinyl pyrrolidone) in a blender. The homogenate was stirred for 1 hour at 4° C. to allow diffusion of cell wall enzymes. Insoluble material was removed by centrifugation at 20,000 g, 30 minutes, 4° C. in the SS34 rotor of the Sorvall RC5B centrifuge. The supernatant was passed through glasswool, and brought to 90% ammonium sulphate saturation by addition of solid ammonium sulphate (60.3 g/100 ml). The mixture was stirred for 40 min at 4° C., and the precipitated proteins collected by centrifugation (38,000 g, 30 minutes, 4° C.). The ammonium sulphate precipitated proteins were stored at −20° C. without resuspension.

Step 5: S-sepharose Cation Exchange Chromatography

0–90% ammonium sulphate precipitated proteins were resuspended in 10 ml 50 mM sodium acetate buffer, pH 5.3 with 0.2 M NaCl (Buffer A) containing 1 mM EDTA, 20 μg/ml chymostatin, 1 mM PMSF. The resuspended pellet was dialysed for 2 hours against 2.5 l of Buffer A using 3,500 M-cut off dialysis tubing. The sample was diluted with 50 mM sodium acetate buffer pH 5.3, 1 mM EDTA to bring the conductivity down to a suitable value for loading onto the S-Sepharose column. The sample was centrifuged at 38,000 g for 15 minutes, 4° C., then loaded onto a 7 ml S-Sepharose Fast Flow column (Pharmacia) equilibrated in Buffer A. The column was washed with Buffer A (flow rate 1 ml/minute) until all unbound proteins were removed. Bound proteins were eluted with a 0–100% gradient of Buffer B (as Buffer A, but with 1 M NaCl) over 10 column volumes. Fractions (2 ml) were collected and assayed for XET activity.

Step 6: Concanavalin A Affinity Chromatography

Fractions from S-sepharose ion exchange chromatography with high XET activity were pooled and stored at −20° C. Prior to concanavalin chromatography, the fractions were brought to 1 mM MgCl$_2$ and MnCl$_2$. The S-Sepharose pool was centrifuged and the supernatant loaded onto a Concavalin-A column equilibrated in 50 mM sodium acetate buffer pH 5.7 containing 0.2 M NaCl, 1 mM MgCl$_2$, 1 mM CaCl$_2$ and 1 mM MnCl$_2$ (Buffer C). Bound proteins were eluted from the column with a single step elution with Buffer D (as Buffer C plus 0.5 methyl α-D-mannopyranoside). Fractions collected were assayed for XET activity.

Step 7: N-terminal Amino Acid Sequencing

Samples from the Concanavalin A column with high XET activity were separated according to apparent molecular weight on a 15% SDS polyacrylamide gel. After electrophoresis, proteins were transferred onto the Problott™ membrane (transfer buffer: 10 mM CAPS pH 11 in 10% methanol). The Problott™ membrane was stained in 0.1% Coomassie Brilliant Blue R250 in 1% acetic acid, 40% methanol and destained in 50% methanol. A single band (i.e. the protein had been successfully purified to homogeneity) of approximate $M^r$36,000 was visible; this was excised and subjected to N-terminal amino acid sequencing on an ABI model 475 protein sequencer. The sequence determined (Seq ID No. 33) was: GYPRRPVDVPFWKNY. The level of the sequence was consistent with the intensity of the stained protein band.

In another aspect therefore, the invention provides a substantially pure polypeptide with xyloglucan endotransglycosylase (XET) activity with an apparent molecular weight of 36 kDa, as judged by SDS-PAGE.

Preferably the enzyme is obtainable from tomato plants, most preferably from the pericarp of green tomato fruit, and preferably has substantially the N-terminal amino acid sequence (Seq ID No.33) GYPRRPVDVPFWKNY.

The enzyme is preferably purified by one or more of ammonium sulphate precipitation, ion exchange chromatography and/or concanavalin A affinity chromatography.

Example 4

Expression of XET in Tomato

The XET assay described above has been used to monitor XET activity throughout the tomato plant (var. Moneymaker). Extracts (0.2M phosphate) were prepared from root, leaf and petiole segments isolated from different parts of the growing plant and fruit at four stages of development and three stages of ripening. Highest XET activity was recorded in extracts prepared from petioles isolated from the top of the growing plant and developing (small green) fruit, consistent with XETs involvement in plant growth.

Total RNA was extracted from different parts of the tomato plant using a Qiagen extraction procedure. tXET-B1

(tomato XET clone B1) transcript levels were determined by RNAse protection analysis. An antisense tXET-B1 specific probe was synthesised by incubating HindIII linearised ptXET-B1 plasmid with 1 μl T3 RNA polymerase in the presence of 0.5 mM rATP/rGTP/rCTP, 5 nM UTP, 50 μCi$^{32}$P-UTP (800 Ci/mmol), 1 μl RNase inhibitor and 2 μl reaction buffer (Ambion probe synthesis kit) in a final reaction volume of 20 μl for 1 hour at 25° C. Following DNase digestion and phenol/chloroform extraction, probe was recovered by ethanol precipitation. $10^5$ cpm labelled probe was incubated with 5 μg total RNA and RNase protection analysis carried out using an RPAII kit supplied by Ambion. Protected probe was quantified by denaturing gel electrophoresis followed by analysis on a Molecular Dynamics PhosphorImager. Highest levels of tXET-B1 transcripts were detected in fruit pericarp, with levels in increasing through ripening and peaking in pink fruit. Maximum levels in stem (equivalent to levels seen in mature green fruit) were found approximately 10 cm from the top of a 30 cm plant. Lower levels of tXET-B1 transcript were detected in leaf with negligible levels in root. The differences in the patterns of activity and transcript level suggest either that total XET activity is encoded by a set of differentially expressed genes or that selective isolation of isoforms is occurring at 0.2M phosphate. The pattern of expression of tXET-B1 suggests that this isoform may be involved in fruit ripening.

Example 5

Reduction of XET Enzyme Levels in Transgenic Tomato Plants

Figure 7:
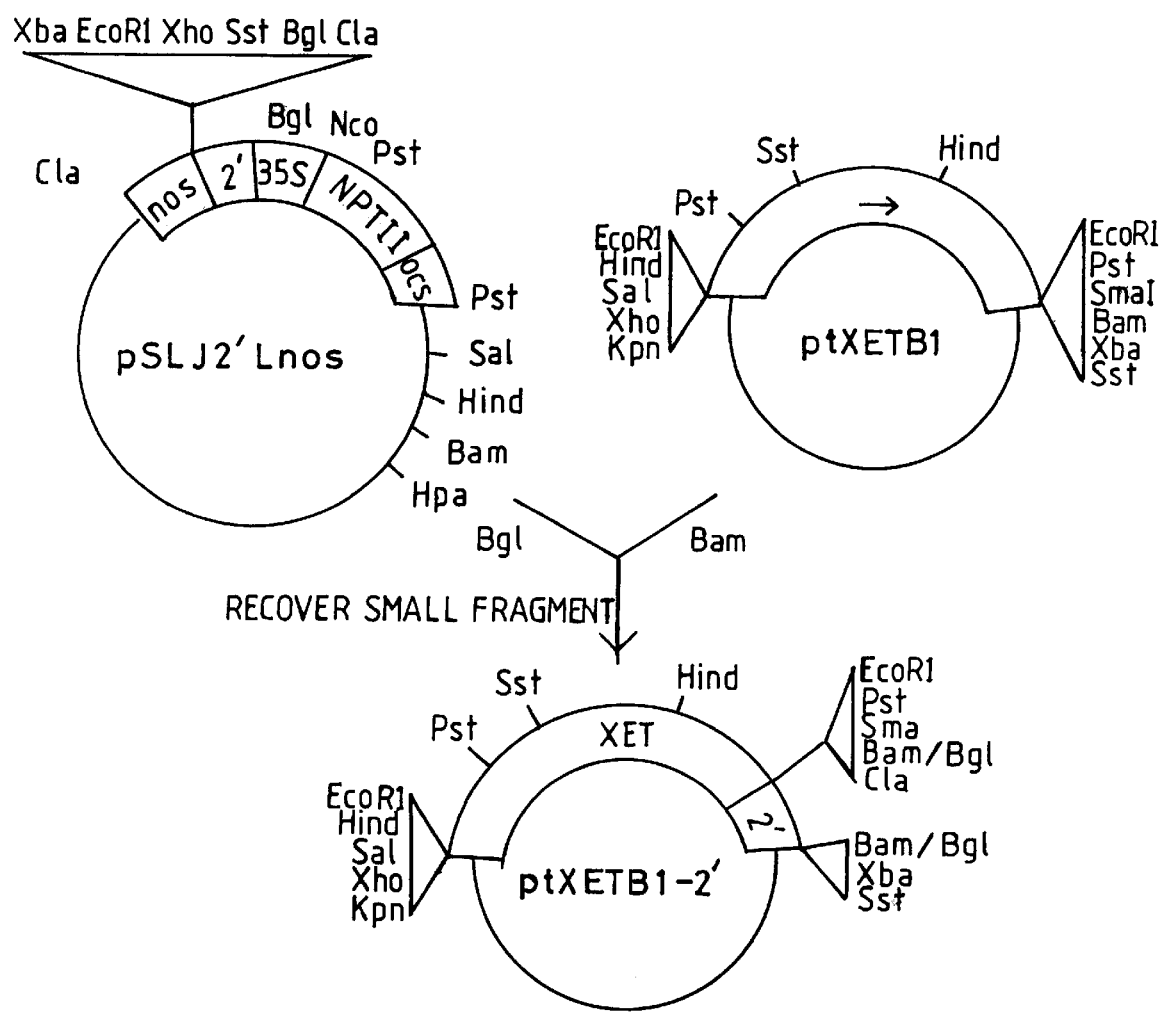
FIGS. 7 and 8 are schematic illustrations of various plasmid constructs.
Figure 8:
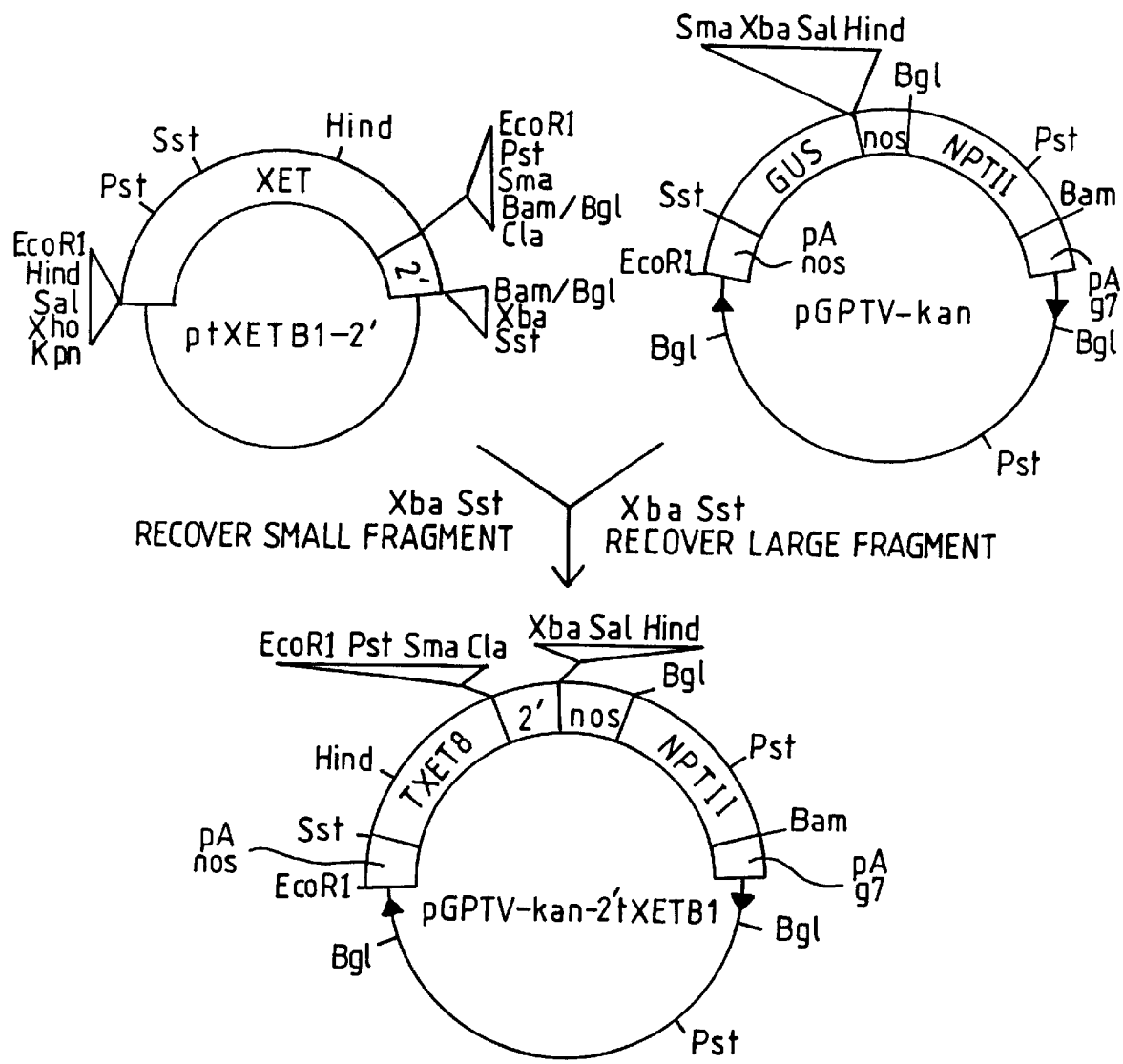

A constitutive 2' mannopine synthase promoter was recovered on a BglII fragment from the plasmid pSLJ2'Lnos, and ligated into the plasmid ptXET-B1. (pSLJ2'Lnos was derived from pSLJ1006 [Jones et al., 1992 transgenic Research 1, 285–297] by replacing the DNA sequence encoding a β-glucuronidase enzyme with a polylinker sequence). This placed the tXET-B1 coding sequence in the antisense orientation with respect to, and downstream of, the 2' promoter (FIG. 7). An Xba - Sst fragment containing the promoter and 798 bp (nucleotides 187 to 984) of tXET-B1 sequence was then cloned into the plant transformation vector, pGPTV-kan (Becker D. et al., 1992, Plant Molecular Biology 20, 1195–1197 and FIG. 8). The resultant plasmid, pGPTV-kan-2'tXET-B1 was used to transform Agrobacterium LBA4404 and the recombinant agrobacterium strain used to infect cotyledonary segments of tomato (variety Moneymaker). Transformed plants were selectively regenerated in the presence of kanamycin. The presence of the transferred DNA was confirmed by PCR amplification of a DNA segment between the primers NPTIIb (5' ATCGGGAGCGGCGATACCGTA 3', Seq ID No. 34) and 8-HS (see above). XET activity was monitored in extracts prepared from pink fruit (15 plants) by the method described above. Levels were reduced by up to approximately 80% in plants transformed with an antisense tXET construct.

What is claimed is:

1. An isolated nucleic acid encoding a polypeptide comprising the amino acid sequence of residues 21–289 of SEQ ID NO:2.

2. The nucleic acid according to claim 1 comprising the nucleotide sequence of SEQ ID NO:1.

3. An isolated nucleic acid encoding a polypeptide comprising the amino acid sequence of residues 19–287 of SEQ ID NO:8.

4. The nucleic acid according to claim 3 comprising the nucleotide sequence of SEQ ID NO:7.

5. The nucleic acid according to claim 1 operably linked to a promoter which is active in a host cell.

6. The nucleic acid according to claim 5, wherein the promoter is not one with which the nucleic acid encoding the polypeptide is naturally associated in a plant.

7. The nucleic acid according to claim 3 operably linked to a promoter which is active in a host cell.

8. The nucleic acid according to claim 7, wherein the promoter is not one with which the nucleic acid encoding the polypeptide is naturally associated in a plant.

9. A vector comprising the nucleic acid in accordance with claim 1.

10. The vector according to claim 9, wherein the vector expresses at least a polypeptide having XET activity when introduced in a host cell.

11. The vector according to claim 10, wherein the vector expresses at least a polypeptide comprising residues 21–289 of SEQ ID NO: 2 when introduced in a host cell.

12. A vector comprising at least a portion of the nucleic acid in accordance with claim 1, wherein said portion is operably linked in antisense orientation to a promoter which is active in a plant cell, wherein said portion of the nucleic acid is of sufficient length to transcribe an antisense nucleotide sequence which reduces XET activity when introduced into a plant cell.

13. A vector comprising the nucleic acid in accordance with claim 3.

14. A vector comprising at least a portion of the nucleic acid in accordance with claim 3, wherein said portion is operably linked in antisense orientation to a promoter which is active in a plant cell, wherein said portion of the nucleic acid is of sufficient length to transcribe an antisense nucleotide sequence and which reduces XET activity when introduced into a plant cell.

15. A host cell into which the nucleic acid in accordance with claim 1 has been introduced, or progeny cells thereof, which progeny cells comprise the nucleic acid.

16. A host cell comprising the vector in accordance with claim 11.

17. A host cell into which the nucleic acid in accordance with claim 3 has been introduced, or progeny cells thereof, which progeny cells comprise the nucleic acid.

18. A method of making a polypeptide having xyloglucan endo-transglycosylase (XET) activity comprising:

introducing the vector in accordance with claim 10 into a host cell;

culturing the host cell, or progeny cells thereof, in culture medium, wherein the polypeptide is expressed; and obtaining the polypeptide from the host cell, the progeny cells, or the culture medium.

19. The method according to claim 18, wherein the host cell is a plant cell or a microbial cell.

20. The method according to claim 19, wherein the host cell is a yeast cell.

21. A method of reducing xyloglucan endo-transglycosylase (XET) activity in a plant or part thereof, comprising introducing into the plant or part thereof the vector in accordance with claim 12, wherein transcription of the vector to produce an antisense transcript reduces XET activity in the plant or part thereof.

22. A method of reducing xyloglucan endo-transglycosylase (XET) activity in a plant or part thereof, comprising introducing into the plant or part thereof the vector in accordance with claim 14, wherein transcription of the vector to produce an antisense transcript reduces XET activity in the plant or part thereof.

23. A transgenic plant produced by introducing the vector in accordance with claim 12 into a plant, or by introducing the vector into a plant part and regenerating a plant from said plant part.

24. A transgenic plant produced by introducing the vector in accordance with claim 14 into a plant or by introducing the vector into a plant part and regenerating a plant from said plant part.

* * * * *